(12) United States Patent
Weis et al.

(10) Patent No.: US 6,207,649 B1
(45) Date of Patent: *Mar. 27, 2001

(54) NUCLEOSIDE ANALOGS AND USES IN TREATING DISEASE

(75) Inventors: Alexander L Weis; Kirupathevy Pulenthiran, both of San Antonio, TX (US)

(73) Assignee: Lipitek International, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/220,307

(22) Filed: Dec. 23, 1998

Related U.S. Application Data

(63) Continuation-in-part of application No. 08/531,875, filed on Sep. 21, 1995, now Pat. No. 6,025,335.

(51) Int. Cl.⁷ ................................................. A61K 31/70
(52) U.S. Cl. .................. 514/44; 536/23.1; 536/25.6; 536/26.23; 536/26.24; 536/26.25; 536/26.26; 536/115; 536/116; 536/117; 536/118; 536/120
(58) Field of Search ................................. 536/25.6, 25.61, 536/27.8, 27.6, 27.81, 28.5, 28.53, 28.54, 28.55

(56) References Cited

U.S. PATENT DOCUMENTS

| | | | | |
|---|---|---|---|---|
| 5,457,187 | * | 10/1995 | Gmeiner et al. | 536/25.3 |
| 5,571,902 | * | 11/1996 | Ravikumar et al. | 536/22.1 |
| 5,608,046 | * | 3/1997 | Cook et al. | 514/44 |
| 6,025,335 | * | 2/2000 | Weis et al. | 514/44 |

FOREIGN PATENT DOCUMENTS

| | | | |
|---|---|---|---|
| 0540741 | 7/1991 | (EP) | 21/4 |
| 0121635 | 10/1984 | (FR) | 19/20 |

OTHER PUBLICATIONS

Holy et al., Coll. of Czech. Chem. Comm; vol. 34, 1969.*

Gulyaeva et al., Coll of Czech Chem. Comm., vol. 44, 1979.*

* cited by examiner

Primary Examiner—James O. Wilson
(74) Attorney, Agent, or Firm—Fulbright & Jaworski, L.L.P.

(57) ABSTRACT

The invention relates to pharmaceutical compositions of nucleoside dimers containing an L-sugar in at least one of the nucleosides.

12 Claims, 20 Drawing Sheets

3'-5' IBA Compounds    5'-5' IBA Compounds    3'-3' IBA Compounds where

A.)

B.)

| f | $R_1$ = α-L-5-fluorouracil, $R_2$ = ß-D-5-fluorouracil |
| X=Me, $CH_2CH_2CN$ |

A)

B)

Synthesis of α-LdU, Cordycepin Dimer L-152

Synthesis of β-L- dC, Cordycepin Dimer L-153

Synthesis of α-LdC, Cordycepin Dimer L-154

Synthesis of α-dA, Cordycepin Dimer L-155

Synthesis of β-LdA, β-D-dA, Dimer L-210

Methox phosphotriesters

Methyl phosphonates

Phosphorodithioates

Silyl Ethers

Sulfonates

Ethylenedioxy ethers

Phosphorothioates

L-113

L-117 thio

L-117

L-120

L-125

L-122

L-124

L-128

BO1   R₁=SATE, R₂=H
BO2   R₁=H, R₂=SATE
BO3   R₁=R₂=SATE

BO4   R₁=H, R₂=SATE
BO5   R₁=R₂=SATE

BO6   R₁=H, R₂=SATE
BO7   R₁=R₂=SATE

SATE:

NUCLEOSIDE ANALOGS AND USES IN TREATING DISEASE

This Application is a continuation-in-part from U.S. patent application Ser. No. 08/531,875, filed on Sep. 21, 1995 now U.S. Pat. No. 6,025,335.

BACKGROUND OF THE INVENTION

1. Field of Invention

This invention relates to novel nucleosides and dinucleoside dimers and derivatives of these compounds, including, L-deoxyribofuranosyl nucleoside phosphodiester dimers in which the sugar moiety of at least one of the nucleosides has an L-configuration. These compounds are highly effective in the treatment of various diseases. They may be used to treat parasitic infections. They may also be used to treat bacterial, viral, and fungal infections, and may also be used to treat cancer.

2. Prior Art

Modified nucleoside analogs are an important class of antineoplastic and antiviral drugs. The present application discloses novel compounds for of this type for use in the treatment of parasitic infections. Due to the extraordinary morbidity and mortality associated with parasitic infections, related research has intensified during the past decade in a desperate search for effective treatments. A safe and effective vaccine still does not exist. Instead, victims must depend upon chemotherapy.

Furthermore, these modified nucleoside analogs may be used to treat bacterial infections, fungal infections, viral infections, and cancer.

These chemotherapeutic agents can be classified into two groups: those that act post-translationally, and those that act by interfering with nucleic acid synthesis.

Most drugs are in the first group, which means that they exert their therapeutic effect by interfering with a cell's protein synthesis, and hence its metabolism (rather than its nucleic acid synthesis). Examples of drugs in this group include: the antifolate compounds (which inhibit dihyrdofolate reductase), and sulfonamide drugs (which inhibit dihydropteroate synthetase. Yet these drugs have serious drawbacks. For example, the protozoan responsible for malaria very quickly develops resistance to these drugs. The reason is that, since resistance occurs through adaptive mutations in successive generations of the parasite, a one or two point mutation is often sufficient to confer resistance. Bacterial, viral, and fungal infections are frequently also susceptible to these types of resistance mutations.

The second group of compounds includes the nucleic acid intercalators such as acridines, phenanthrenes and quinolines. These intercalators partially mimic the biochemical activity of nucleic acids, and therefore are incorporated into a cell's nucleic acid (DNA and RNA), though once incorporated, do not allow further nucleic acid synthesis, hence their effectiveness. At the same time, these intercalators interfere with host nucleic acid synthesis as well, and thus give rise to toxic side effects. Because of the potential for toxic side effects, these drugs can quite often be given only in very small doses. Once again, a resistance pattern may develop. For example, some protozoans are known to develop "cross-resistance," which means that the parasites develop resistance to other classes of drugs even though they were exposed on a different class of drug.

Indeed, all of the currently known drugs or drug candidates utilizing the delivery of cytotoxic pyrimidine or purine biosynthesis inhibitors to invading cells are extremely toxic. Therefore, while drugs of this type—i.e., those that interfere with nucleic acid synthesis-are effective, they lack selectivity. It is this latter parameter that must be maximized in the development of a safe and effective drug. In other words, such a drug would target host tissues that are infected, or cancerous, yet leave the host tissue unchanged.

Recent advances in our understanding of the biochemistry of parasite cells serves as a valuable example regarding the design of effective therapies. One investigator (H. Ginsburg, Biochem. Pharmacol. 48, 1847–1856 (1994)) observed that normal and parasite-infected erythrocytes exhibit significant differences with respect to purine and pyrimidine metabolism in single enzymes, as well as in whole branches of related pathways. The parasite satisfies all of its purine requirements through scavenger pathways; meanwhile, the host cell lacks the enzymes necessary to exploit this pathway, and so therefore must meet its pyrimidine requirements largely through de novo synthesis. Put another way, the parasite is more efficient than normal or host cells since it can synthesize the nucleic acid building blocks.

Other investigators (G. Beaton, D. Pellinqer, W. S. Marshall & M. H. Caruthers, In: *Oligonucleotides and Analogues: A Practical Approach*, F. Eckstein Ed., IRL Press, Oxford, 109–136 (1991)) have established that a malaria-infected erythrocyte is capable of effectively transporting the non-naturally occurring "L-nucleosides" (in contrast to the "D-nucleosides" which are the naturally occurring form) for use in nucleic acid synthesis. Yet, normal mammalian cells are nonpermeable to this class of compounds, which suggests that the L-nucleosides are non-toxic to normal mammalian or host cells. Thus, derivatives of these compounds may be used as highly selective drugs against parasite infection, or against any other type of cell or organism utilizing the L-nucleosides. The chemical modification of the L-nucleosides consists generally of modifying the nucleosides so that they are still recognized by the invading cell or organism's nucleic acid synthetic machinery, and therefore incorporated into a nucleic acid chain, but yet once this incorporation occurs, no further synthesis will take place.

Currently, there are no therapeutic compounds in use that are based on dimers of these nucleoside analogs. While dimers of the naturally occurring D-deoxyribofuranosyl nucleosides are well known, dimers in which one or both nucleosides are of the unnatural L-configuration are much less known, and their use in therapy of neoplastic and viral diseases is unknown.

In the synthesis of DNA-related oligomers, types of nucleoside dimers are synthesized as part of the overall process. These dimers usually include bases from naturally occurring DNA or RNA sequences. There is much known in the art about nucleoside monophosphate dimers. Many of these compounds have been synthesized and are available commercially.

However, these dimers are made from nucleosides containing a sugar moiety in D-configuration.

Reese, C. B., Tetrahedron 34 (1978) 3143 describes the synthesis of fully-protected dinucleoside monophosphates by means of the phosphotriester approach.

Littauer, U. Z., and Soreg, H. (1982) in *The Enzymes*, Vol. XV, Academic Press, NY, p. 517 is a standard reference which describes the enzymatic synthesis of dinucleotides.

Heikkilö, J., Stridh, S., Oberg, B. and Chattopodhyaya, J., Acta Chem. Scand. B 39 (1985) 657–669, provides an example of the methodology used in the synthesis of a variety of ApG nucleoside phosphate dimers. Included are references and methods for synthesis of 3'→5' phosphates and 2'→5' phosphates by solution phase chemistry.

Gait, M., "Oligonucleotide Synthesis", IRL Press, Ltd., Oxford, England, 1984, is a general reference and a useful overview for oligonucleotide synthesis. The methods are applicable to synthesis of dimers, both by solution phase and solid phase methods. Both phosphitetriester and phosphotriester methods of coupling nucleosides are described. The solid phase method is useful for synthesizing dimers.

Gulyawa, V. and Holy, A., Coll. Czec. Chem. Commun 44 613 (1979), describe the enzymatic synthesis of a series of dimers by reaction of 2',-3' cyclic phosphate donors with ribonucleoside acceptors. The reaction was catalyzed by non-specific RNases. The donors are phosphorylated in the 5'-position, yielding the following compounds: donor nucleoside-(3'→5') acceptor nucleoside. Dimers were made with acceptors, β-L-cytidine, β-L-adenosine, and 9(α-L-lyxofuranosyl) adenine. Also, a large number of dimers with D-nucleosides in the acceptor 5'-position were made.

Holy, A., Sorm, F., Collect. Czech. Chem. Commun., 34, 3383 (1969), describe an enzymatic synthesis of β-D-guanylyl-(3'→5')-β-L-adenosine and β-D-guanylyl-(3'→5')-β-L-cytidine.

Schirmeister, H. and Pfleiderer, W., Helv. Chim. Acta 77, 10 (1994), describe trimer synthesis and intermediate dimers, all from β-D-nucleosides. They used the phosphoramidite method which gave good yields.

Thus, dimers with L-deoxyribofuranosyl moieties in any position are new, as are dimers with L-ribofuranosyl moieties bonded to the 3'-position of the phosphate internucleotide bond.

Modified nucleoside analogues represent an important class of compounds in the available arsenal of antineoplastic and antiviral drugs. The anticancer agents 5-fluorodeoxyuridine (floxuridine), cytarabine and deoxycoformycin and the antiviral drugs 3'azidodeoxythymidine (AZT), dideoxycytidine (ddC), dideoxyinosine (ddI), acyclovir, 5-iododeoxyuridine (idoxuridine) fludarabine phosphate and vidarabine (adenine arabinoside/ara A) are representative of this class of monomeric nucleoside-derived compounds which are used therapeutically.

More recently, "antisense" oligonucleotide analogues with modified bases and/or phosphodiester backbones have been actively pursued as antiviral and antitumor agents. While no clinically approved drug has yet emerged from this class of compounds, it remains a very active field of research. Recently, antipodal L-sugar-based nucleosides also have found application as potent antiviral agents because they can inhibit viral enzymes without affecting mammalian enzymes, resulting in agents that have selective antiviral activity without concomitant mammalian cytotoxicity. Most naturally occurring nucleosides have the D-configuration in the sugar moiety. While the chemical properties of L-nucleosides are similar to those of their β-D-enantiomers, they exhibit very different biological profiles in mammalian cells and do not interfere with the transport of normal D-nucleosides. For example, β-L-uridine is not phosphorylated at the 5'-position by human prostate phosphotransferase, which readily phosphorylates the enantiomeric β-D-uridine. Apparently, L-nucleosides are not substrates for normal human cell kinases, but they may be phosphorylated by viral and cancer cell enzymes, allowing their use for the design of selective antiviral and anticancer drugs. Oligonucleotides based on L-nucleosides have been studied previously. Octamers derived from α- and β-L-thymidine were found resistant to fungal nucleases and calf spleen phosphodiesterase, which readily degrades the corresponding β-D-oligonucleotide. Fujimory, et al., S.

Fujimory, K. Shudo, Y. Hashimoto, J. Am. Chem. Soc., 112, 7436, have shown that enantiomeric poly-α-DNA recognizes complementary RNA but not complementary DNA. This principle has been used in the design of nuclease-resistant antisense oligonucleotides for potential therapeutic applications.

Thus, L-nucleoside-based compounds have potential as drugs against neoplastic, fungal, and viral diseases, as well as against parasitic infections.

While L-sugar-derived nucleosides and their oligonucleotides have been widely evaluated for such activities, little is known regarding the biological activities of shorter oligomers such as dimers obtained by L-nucleoside substitution.

This invention comprises novel L-nucleoside-derived therapeutic antitumor, antiviral, antibacterial, antifungal, and antiparasitic agents. Novel L-nucleoside-derived dinucleoside monophosphates, based on L-α-5-fluoro-2'-deoxyuridine showed a remarkably high potency activity profile in in vitro anti-cancer assays, with indications of unique mechanisms of action, including inhibition of telomerase. Therefore, the L-nucleosides can serve as building blocks for new drugs with the special advantage of low toxicity.

SUMMARY OF THE INVENTION

A further embodiment of the present invention is the administration of a therapeutically effective amount of the compounds of the present invention for the treatment of cancer, viral infections, parasitic infections, fungal infections, and bacterial infections.

Other and further objects, features and advantages will be apparent from the following description of the present preferred embodiments of the invention given for the purposes of disclosure when taken in conjunction with the accompanying drawings.

BRIEF DESCRIPTION OF THE DRAWINGS

FIG. 14A shows the methoxyphosphotriesters, methylphosphonates, phosphorodithioates, and silylethers. FIG. 14B shows the sulfonates, ethylenedioxyesters, and phosphorotioates that can be used as the backbone.

FIG. 15A shows a schematic representation of the dinucleotide dimers: GCI-1077, GCI-1079, GCI-1085, GCI-1086, FUdR, L-145, L-147, L-146 and L-144.

FIG. 15B shows a schematic representation of the dimers: L-133, L-138, GCI-1007, GCI-1018, G-1027, GCI-1030, GCI-1032, GCI-1033, GCI-1034, GCI-1036, GCI-1037, GCI-1066, GCI-1069, and GCI-1070.

FIG. 15C shows a schematic representation of the dimers: L-113, L-117thio, L-117, L-120, L-125, L-122, L-124, and L-128.

FIG. 15D shows a schematic representation of the dimers: L-101, L-103, L-103thio, L-103CN, L-107, L-109, L-110, L-111, and L-112.

FIG. 15E shows a schematic representation of dimers: B01, B02, B03, B04, B05, B06, and B07.

Certain features of the invention may be exaggerated in scale or shown in schematic form in accordance with the customary practices in the biochemical arts.

DETAILED DESCRIPTION OF THE PREFERRED EMBODIMENTS

It is readily apparent to one skilled in the art that various substitutions and modifications may be made to the invention disclosed in this Application without departing from the scope and spirit of the invention.

Figure 1:
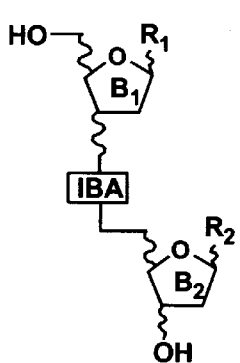
FIG. 1 is a schematic representation of examples of the dinucleotide dimers of the present invention.
Figure 1:
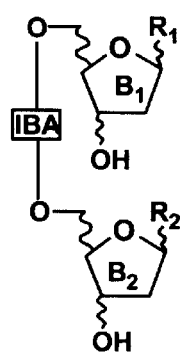
Figure 1:
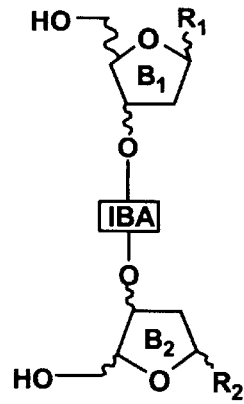
Figure 1:
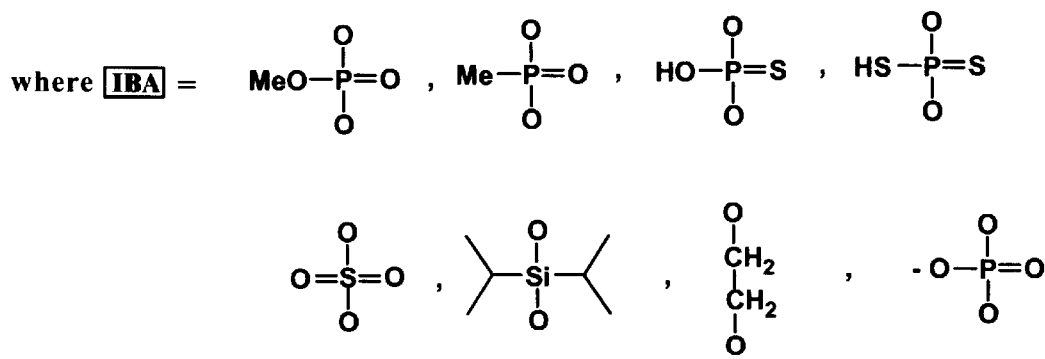
Figure 2:
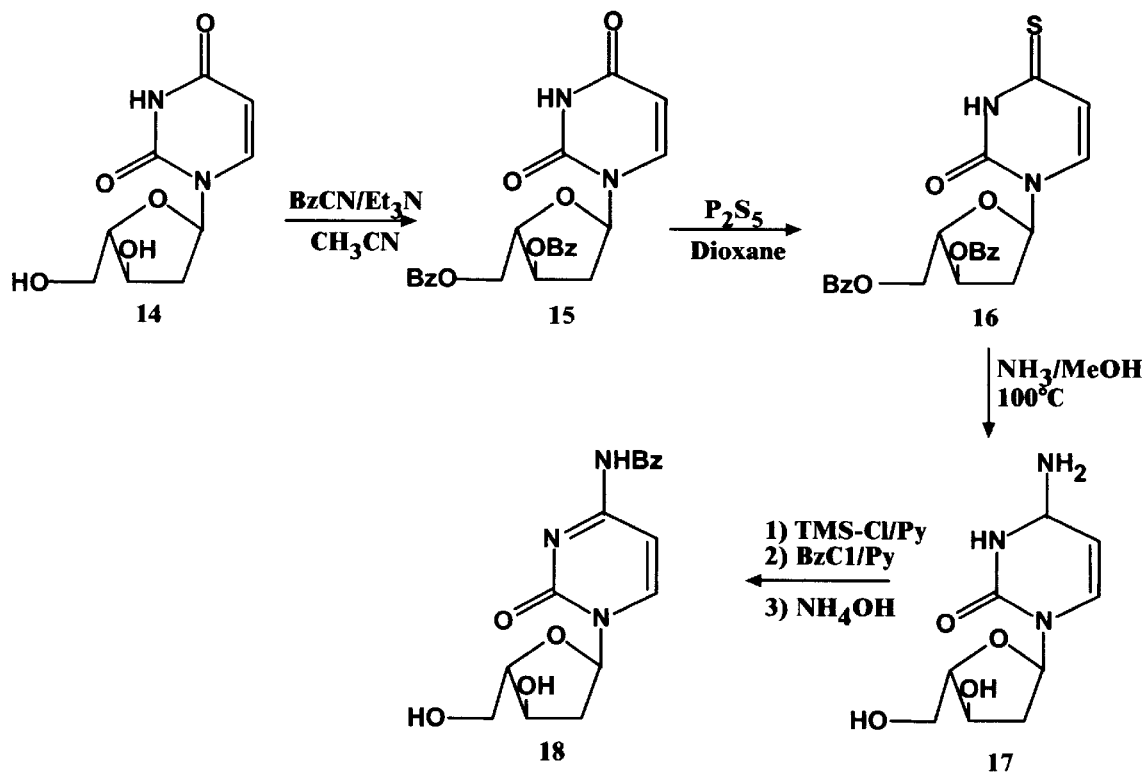
FIG. 2 is a schematic representation of part of the synthesis scheme of compound $N^4$benzoyl-2'-deoxy-alpha-Lcytidine, an intermediate in the synthesis of the dimers.
Figure 3:
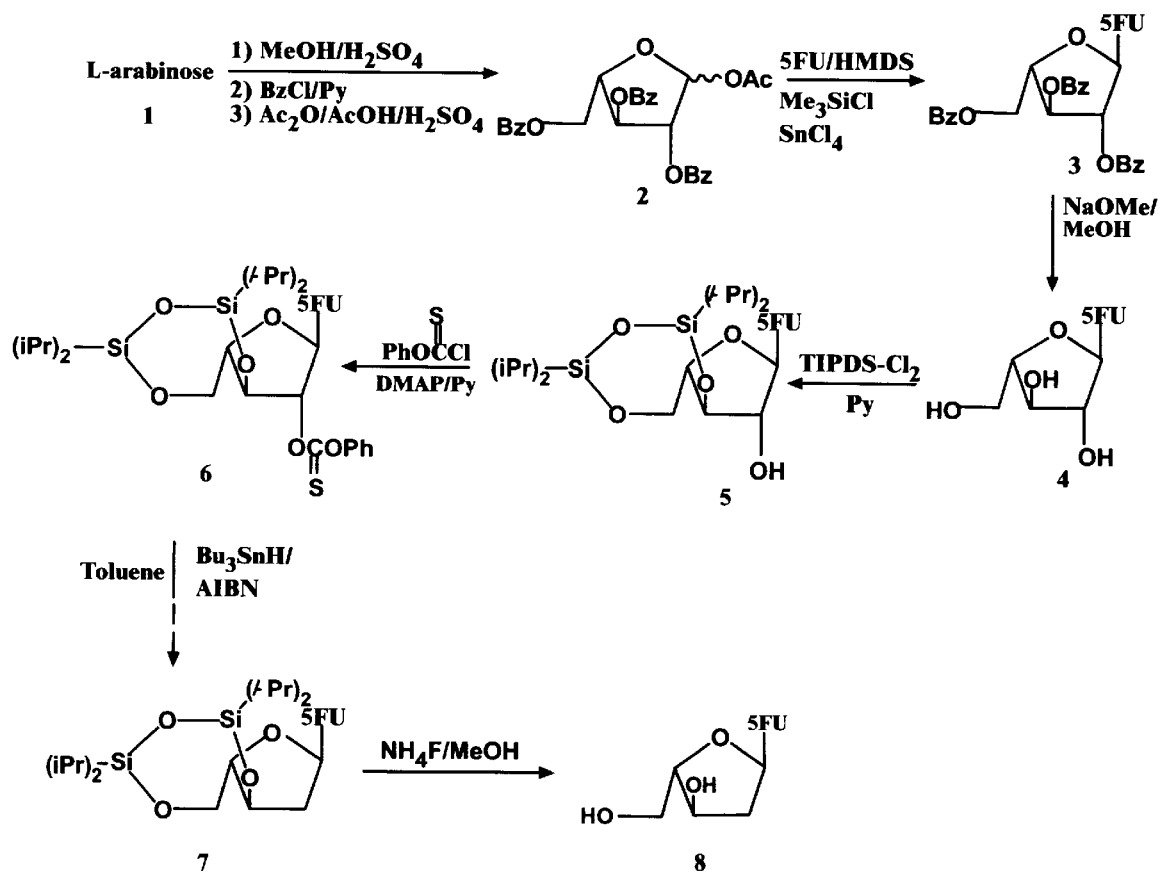
FIG. 3 is a schematic representation of part of the synthesis scheme for compounds of the present invention (2'-deoxy-alpha-L-5-fluoriuridene compound).
Figure 4:
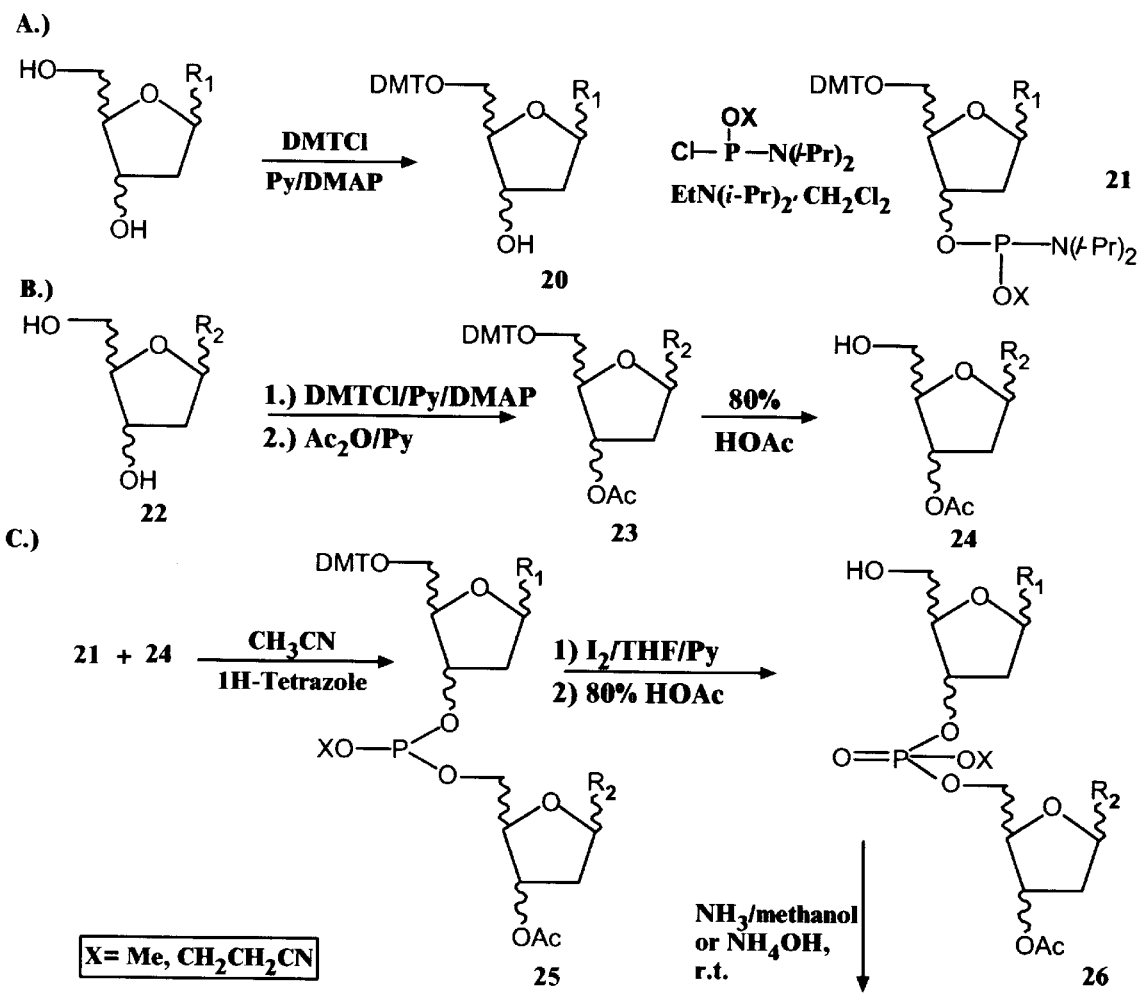
FIG. 4 is a schematic representation of the synthesis of a specific series of alpha-beta or beta-alpha dimers.
Figure 4:
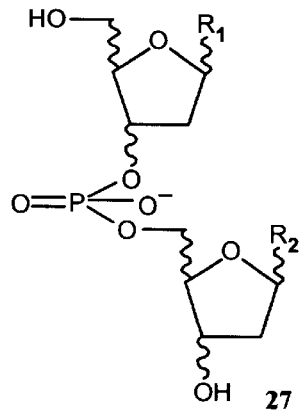
Figure 5:
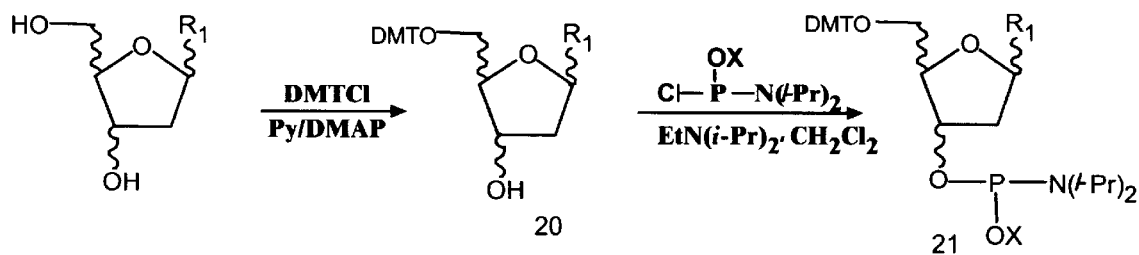
FIG. 5 is a schematic representation of the synthesis of an α-L-5 fluorouracil-β-D-5 fluorouracil.
Figure 5:
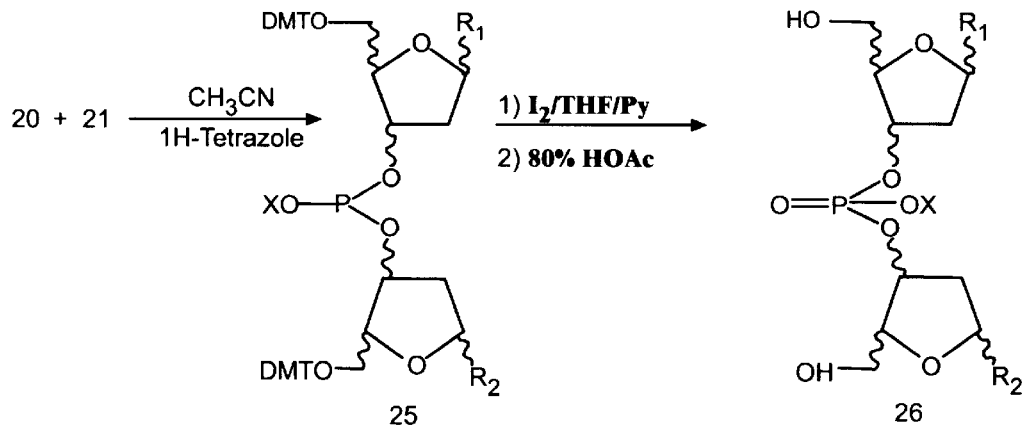
Figure 5:
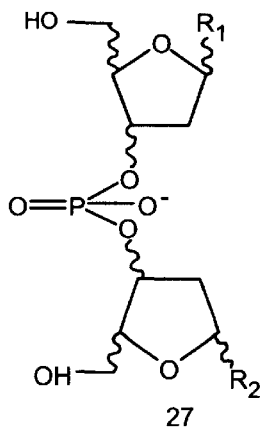
Figure 6:
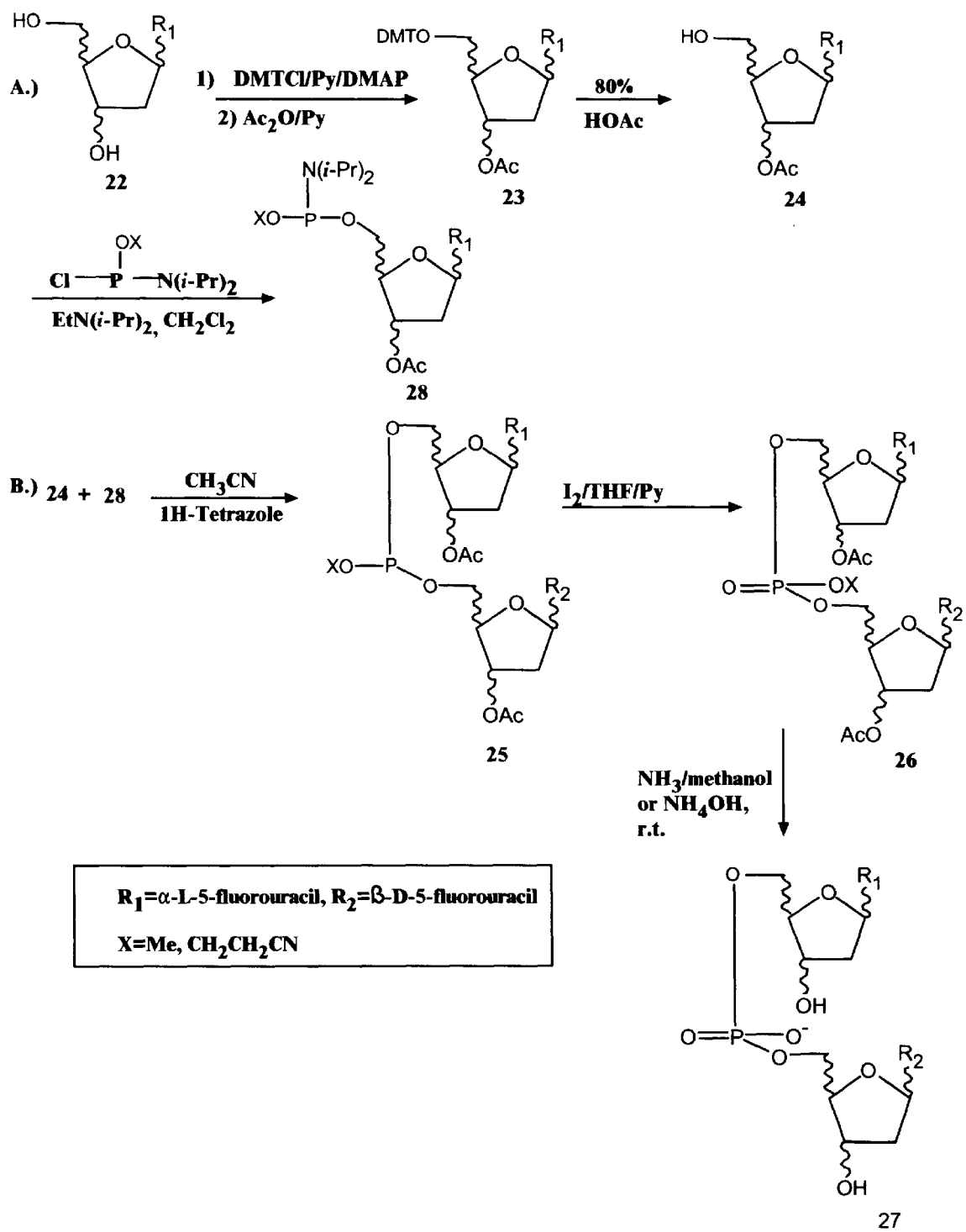
FIG. 6 is a schematic representation of an alternative pathway for the synthesis of α-L-5 fluorouracil-β-D-5 fluorouracil.
Figure 7:
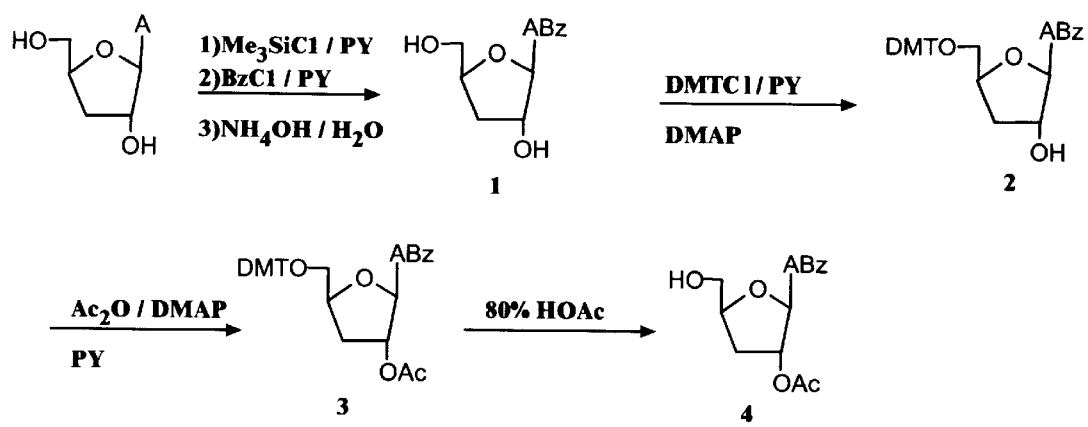
FIG. 7 is a schematic representation for the synthesis of dimer compounds, L-150.
Figure 7:
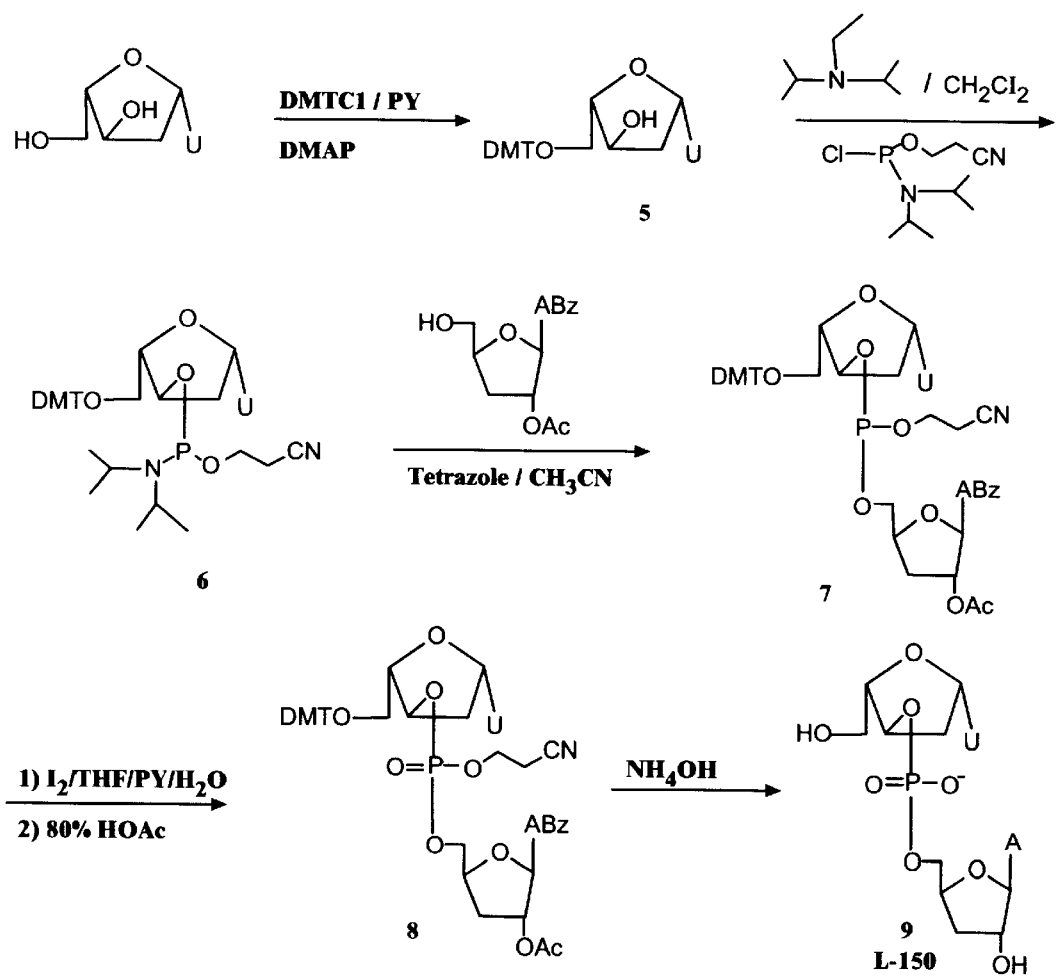
Figure 8:
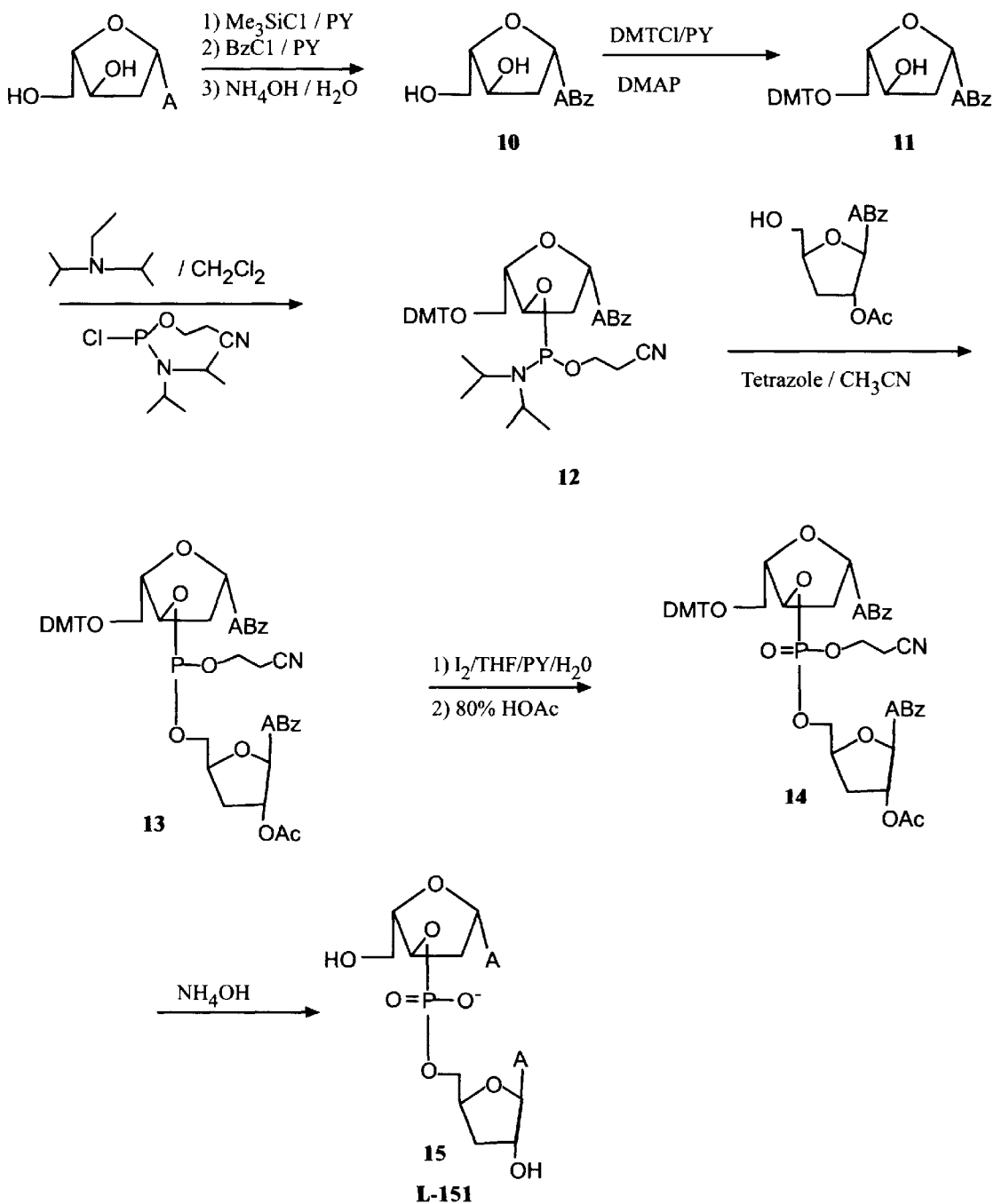
FIG. 8 is a schematic representation of a synthesis pathway for a dimer compound. L-151.
Figure 9:
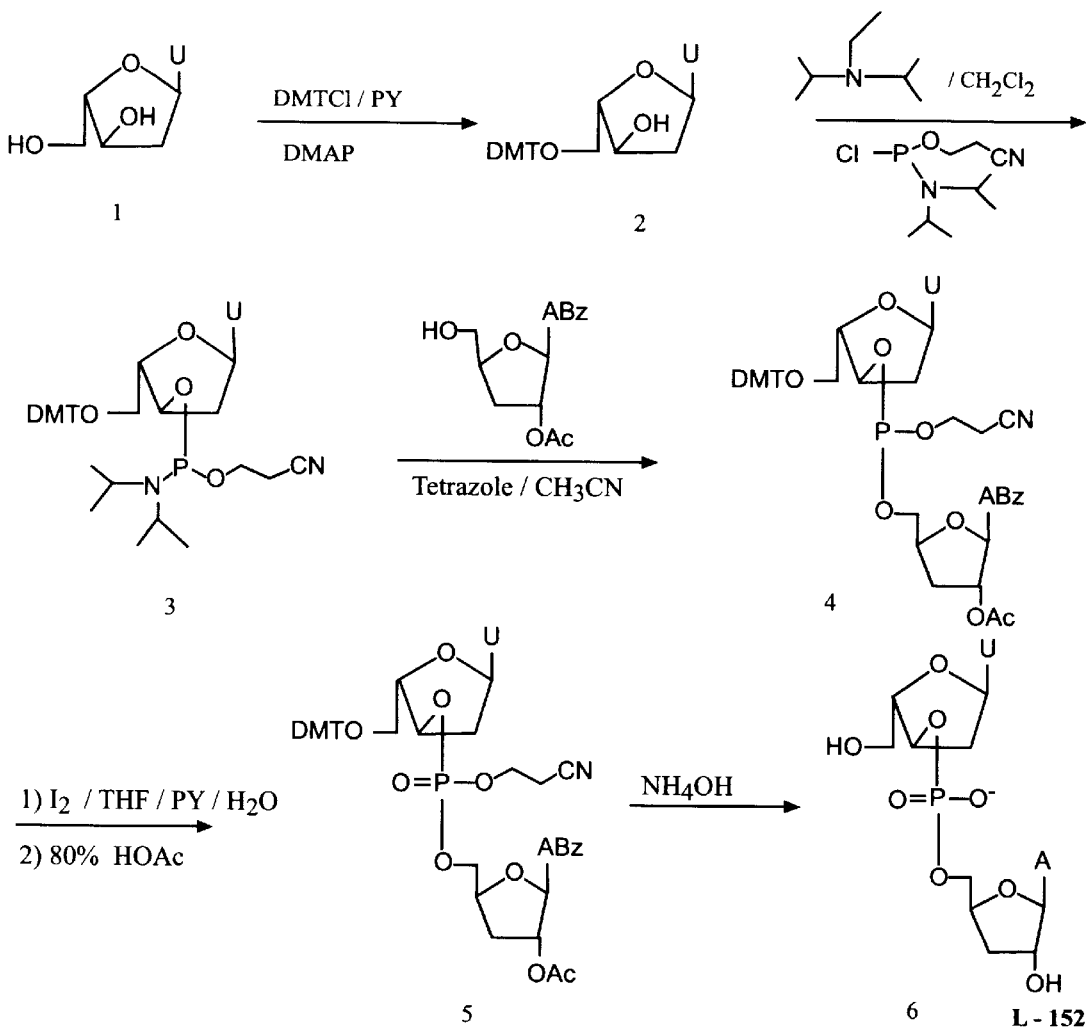
FIG. 9 is a schematic representation of the synthesis pathway of α-L-dU, Cordycepin dimer, L-152.
Figure 10:
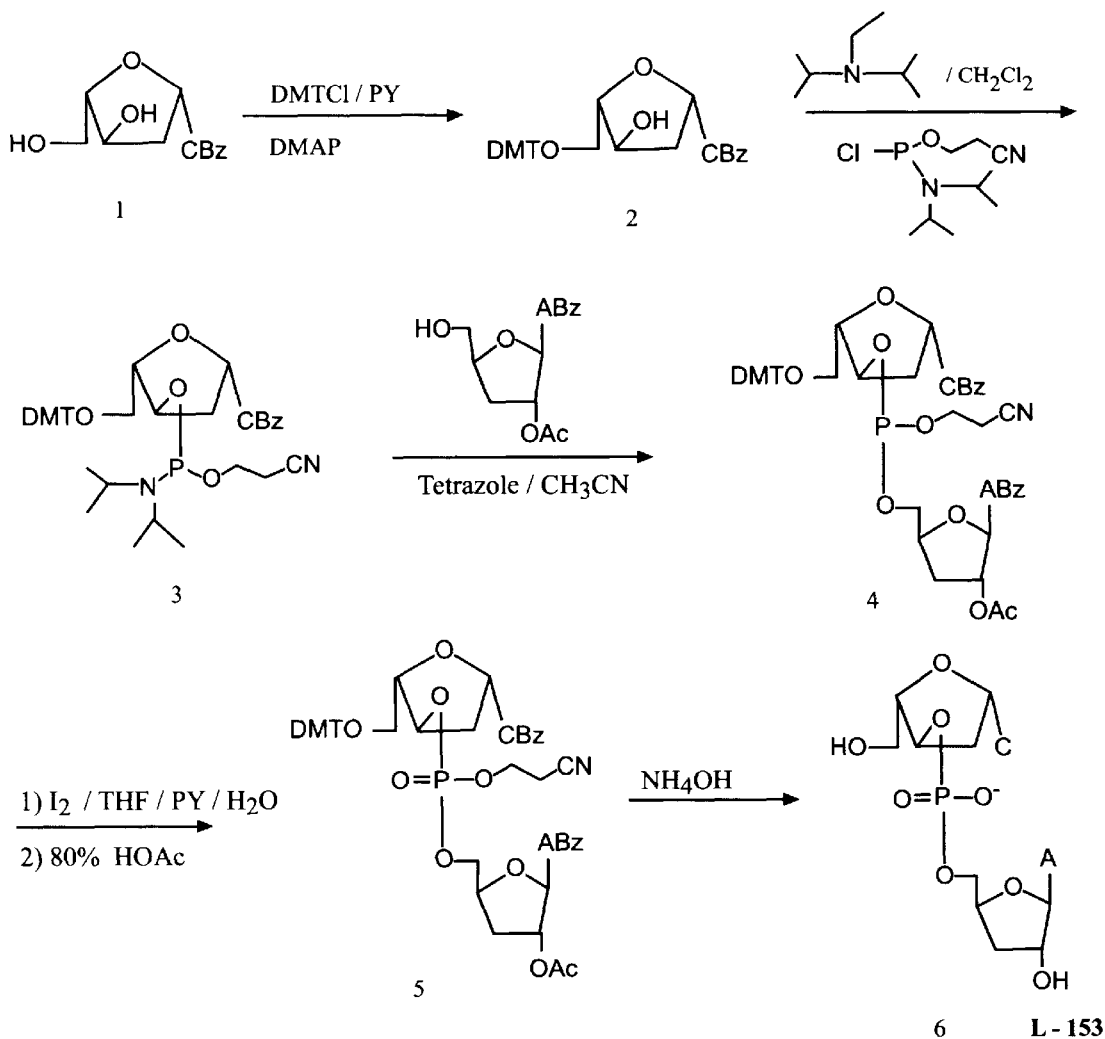
FIG. 10 is a schematic representation of the synthesis of β-L-dC, Cordycepin dimer, L-153.
Figure 11:
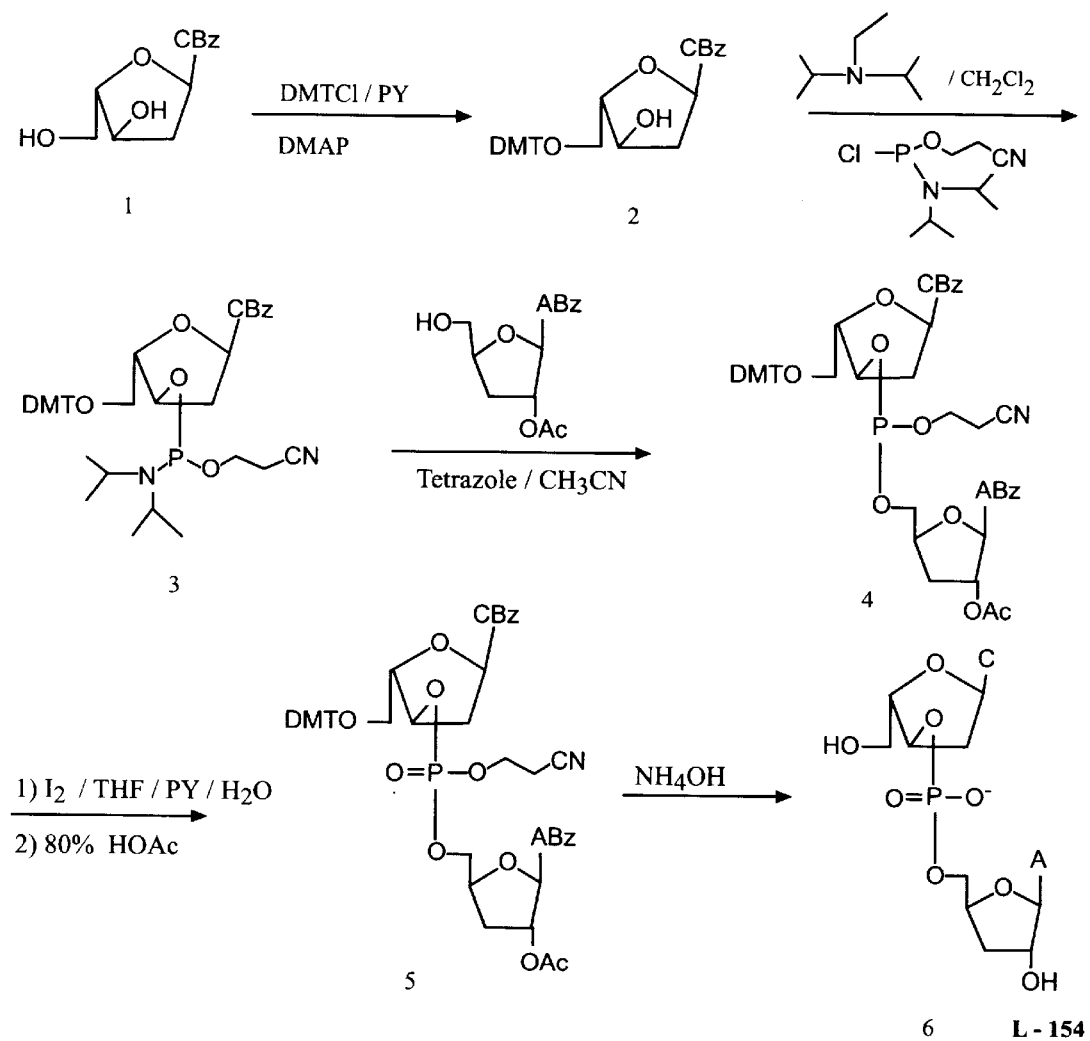
FIG. 11 is a schematic representation of the synthesis pathway of α-L-dC, Cordycepin dimer, L-154.
Figure 12:
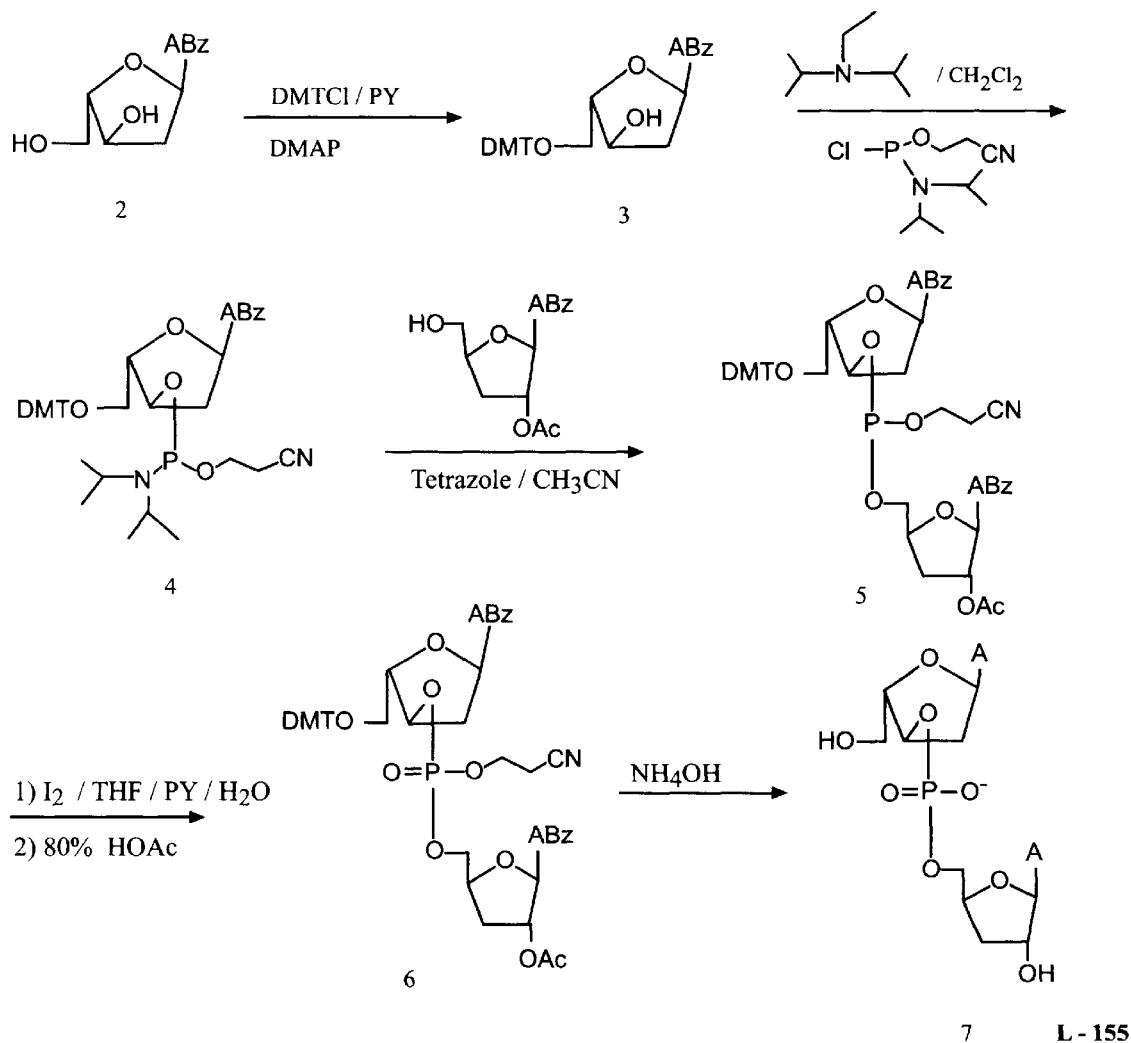
FIG. 12 is a schematic representation of the synthesis pathway of α-dA, Cordycepin dimer, L-155.
Figure 13:
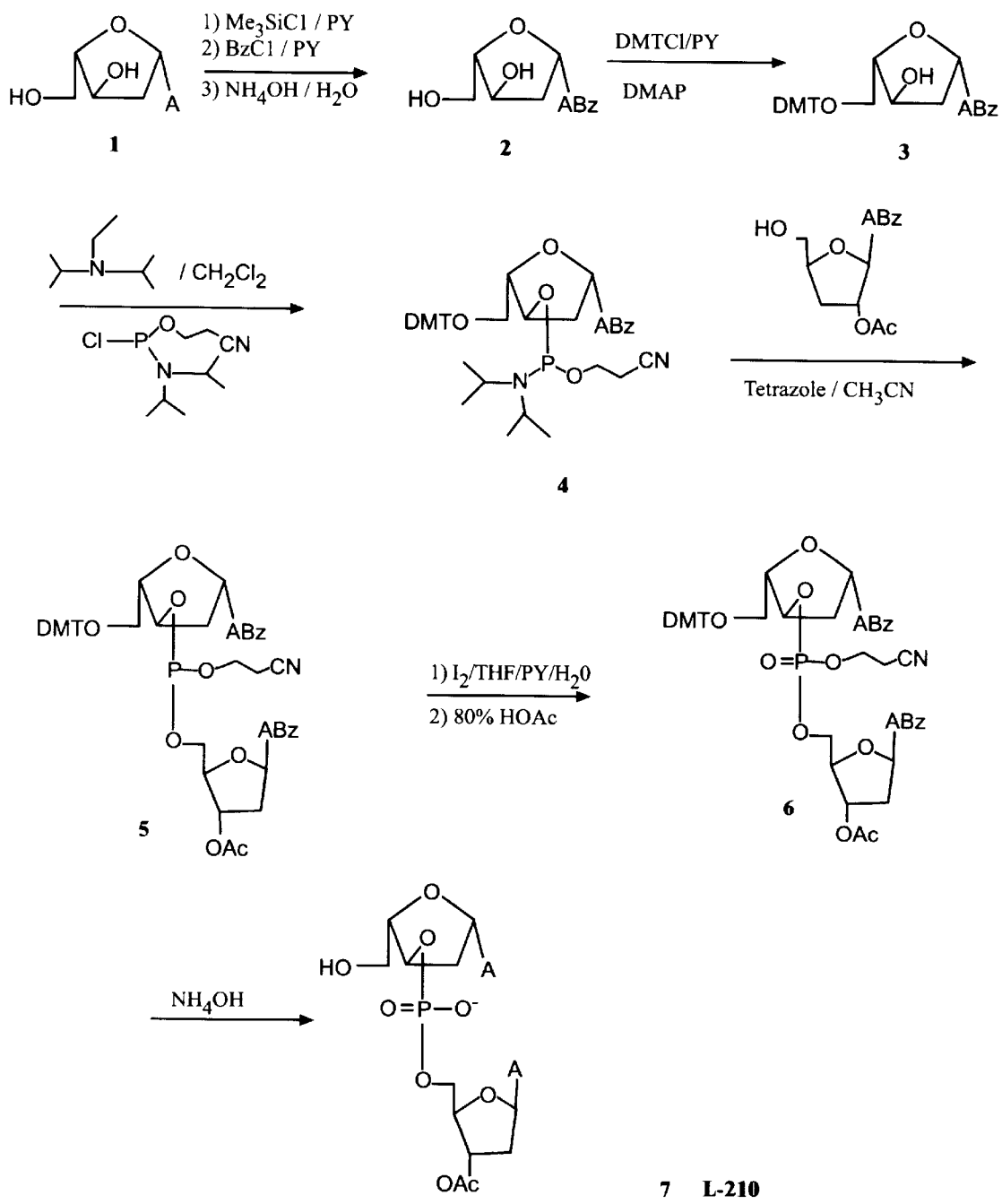
FIG. 13 is a schematic representation of the synthesis of -L-β-dA, β-D-dA dimer, L-210.
Figure 14A:
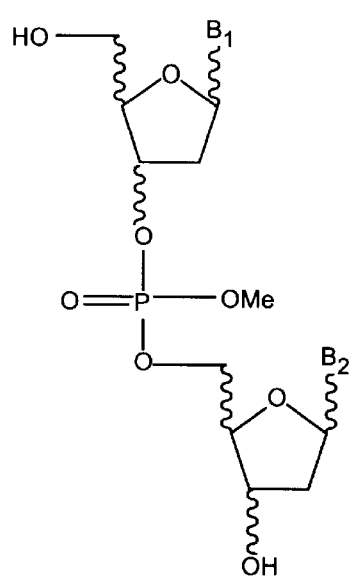
FIGS. 14A and 14B are schematic representations of dinucleoside phosphate dimers containing alternative backbones.
Figure 14A:
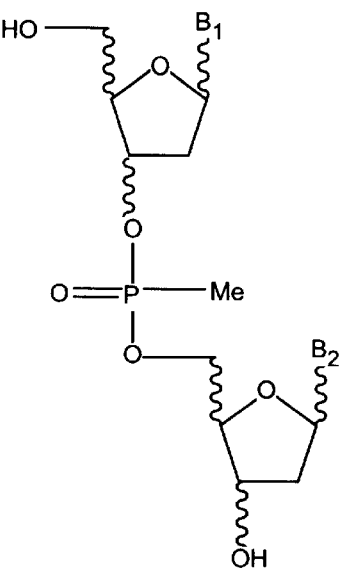
Figure 14A:
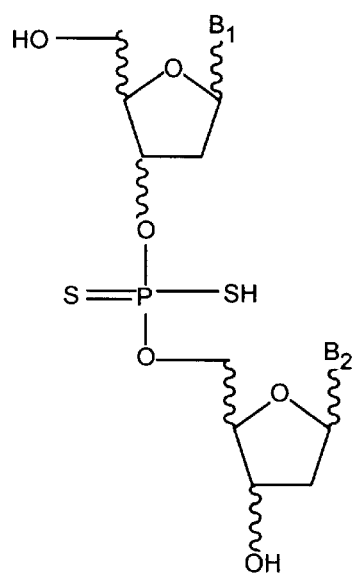
Figure 14A:
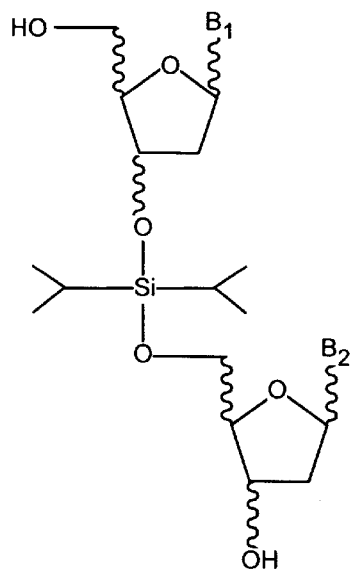
Figure 14B:
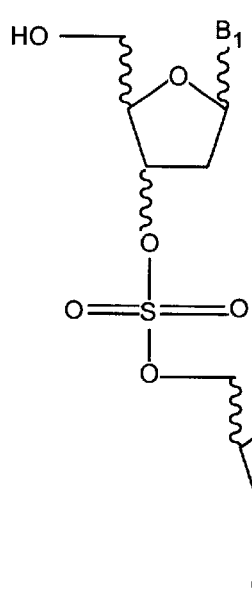
Figure 14B:
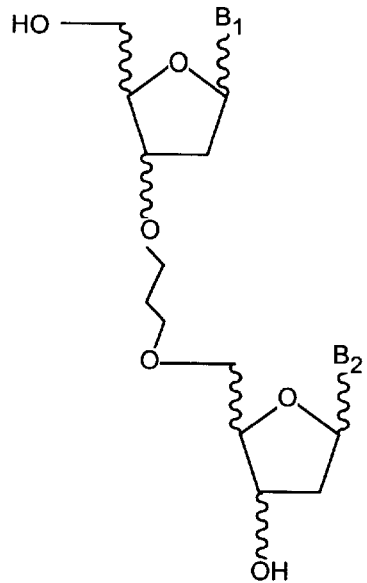
Figure 14B:
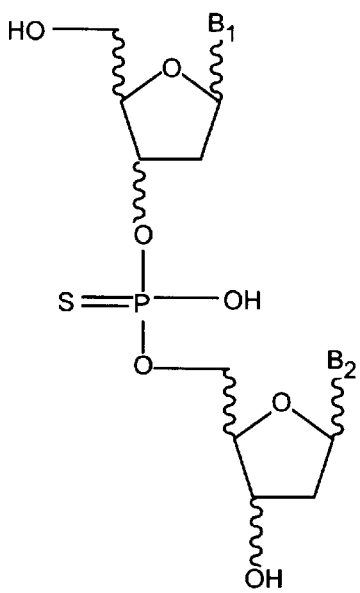
Figure 15A:
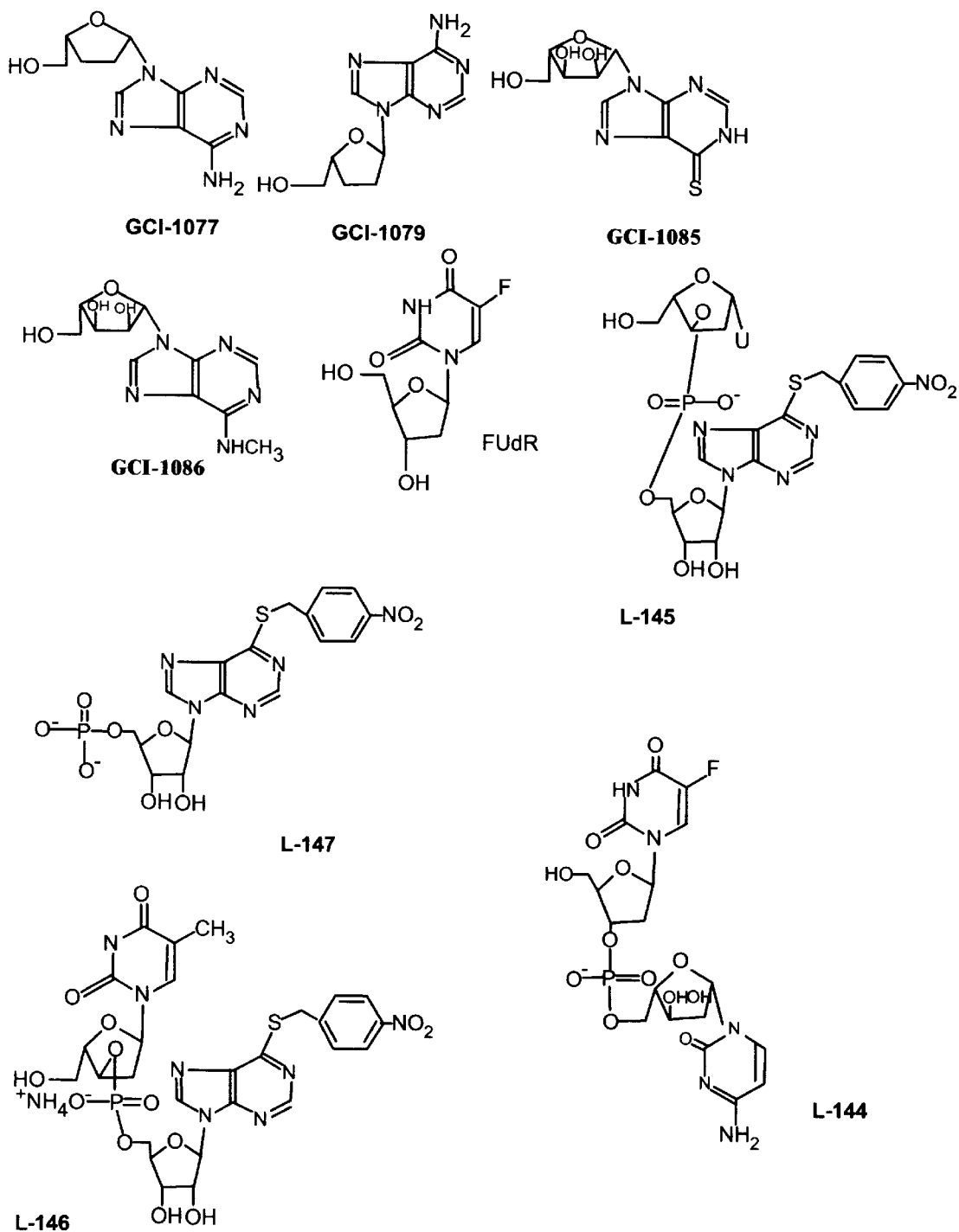
FIGS. 15A, 15B, 15C, 15D, and 15E are schematic representations of dinucleoside phosphate dimers used in the examples.
Figure 15B:
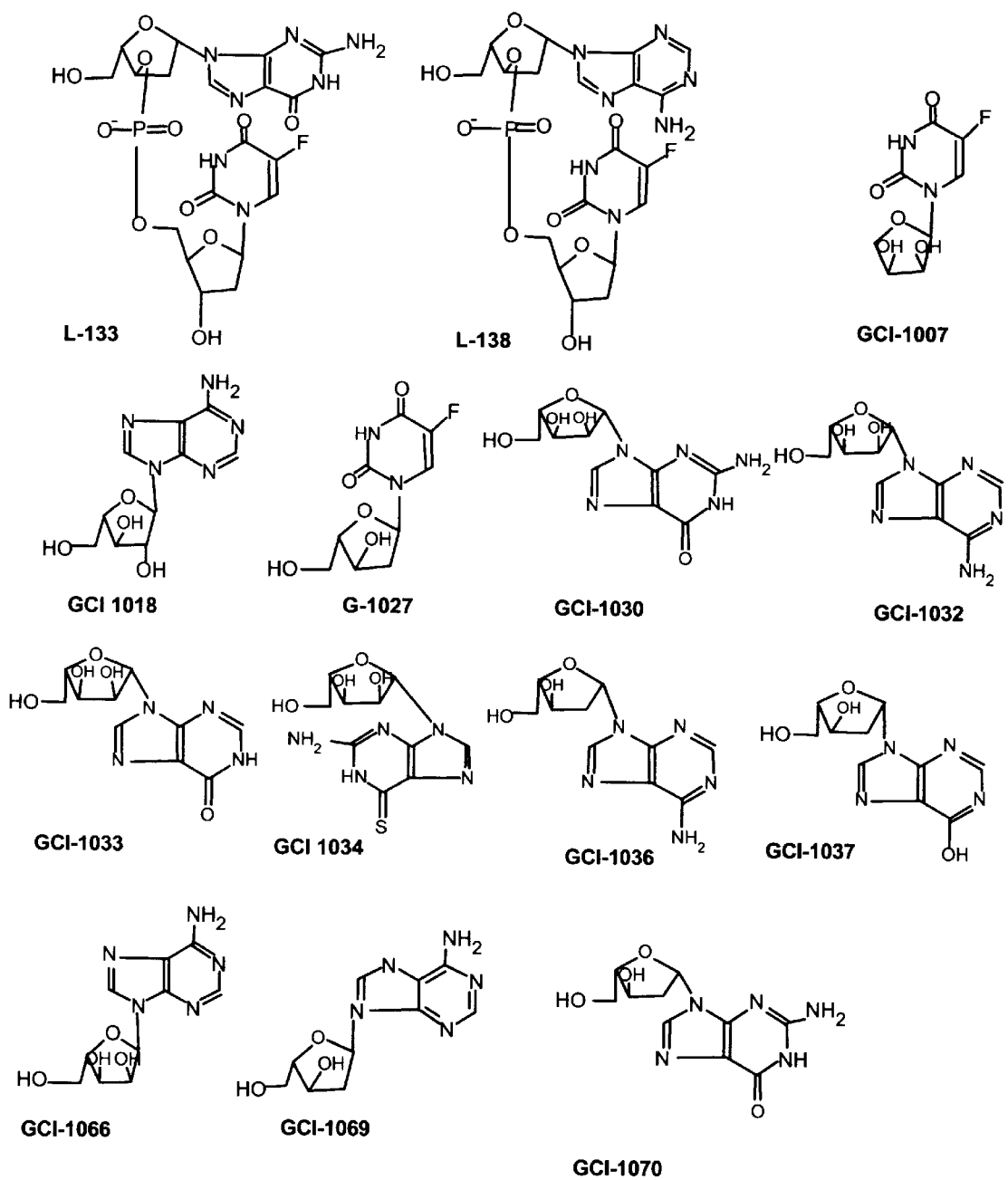
Figure 15C:
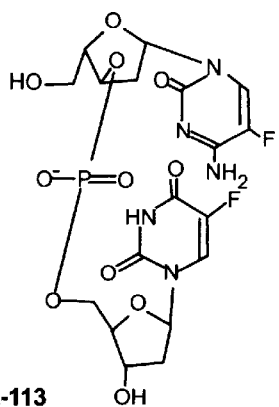
Figure 15C:
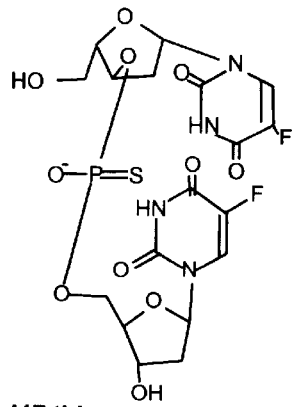
Figure 15C:
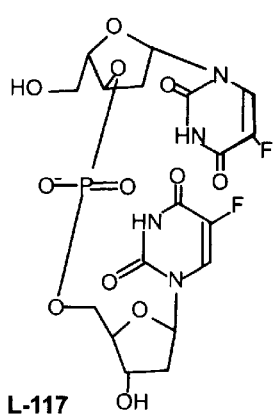
Figure 15C:
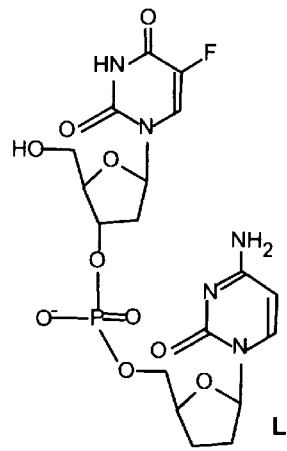
Figure 15C:
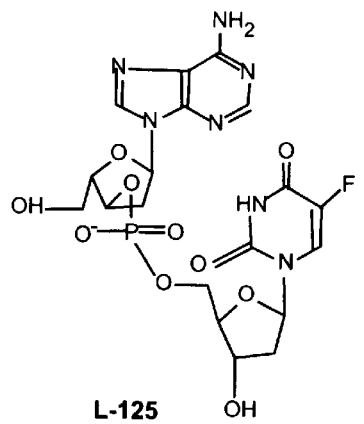
Figure 15C:
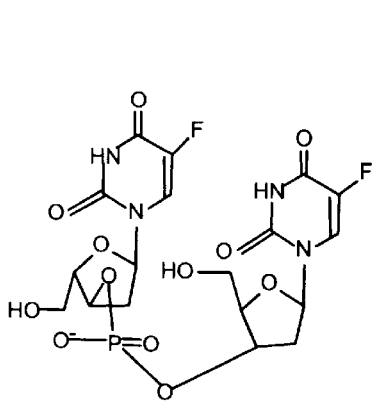
Figure 15C:
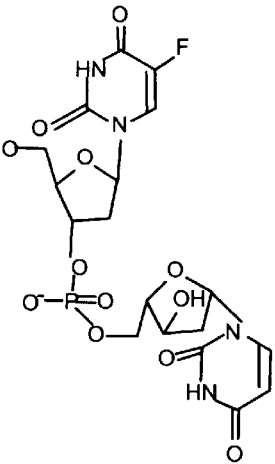
Figure 15C:
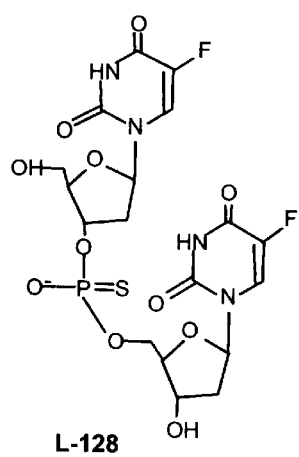
Figure 15D:
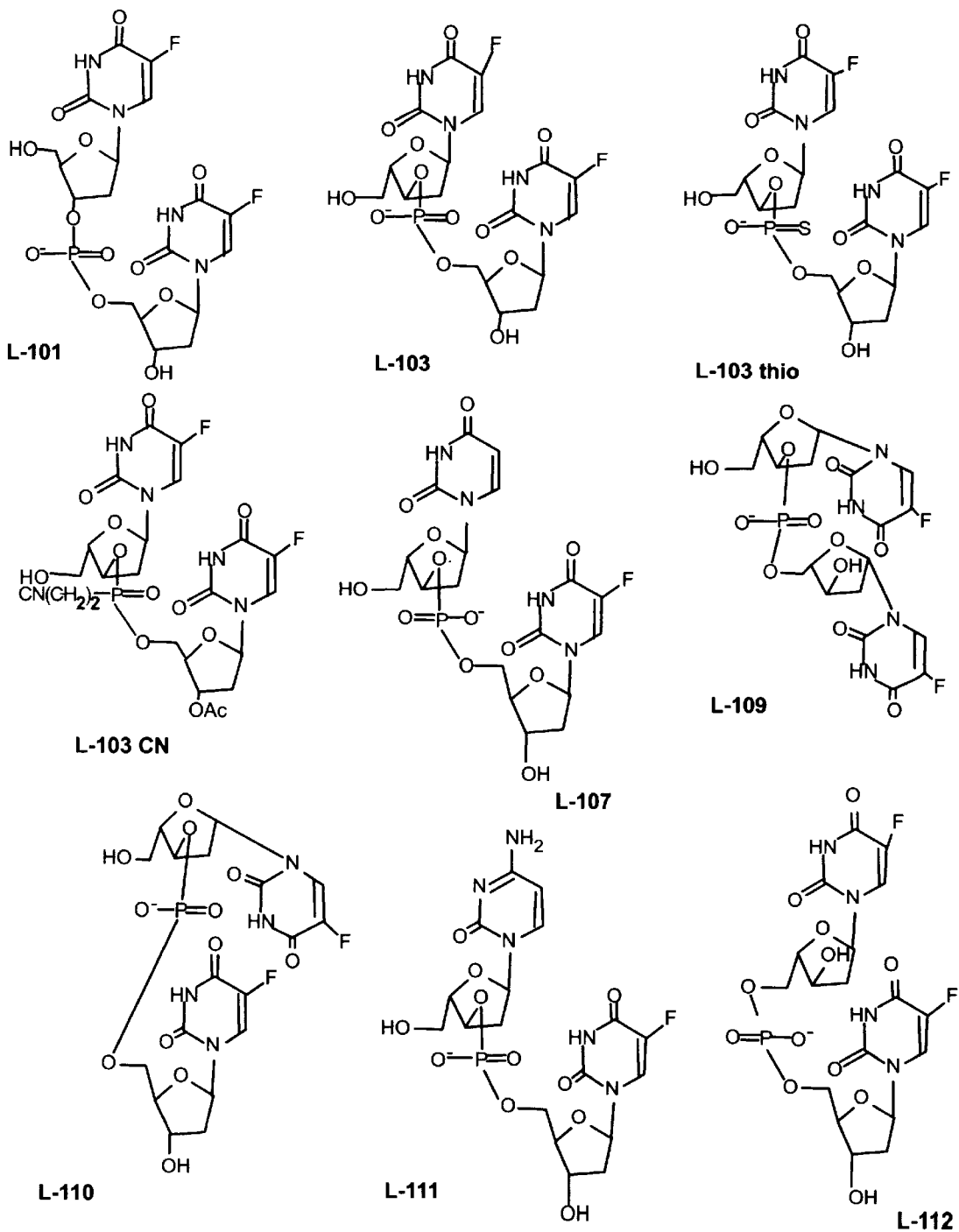
Figure 15E:
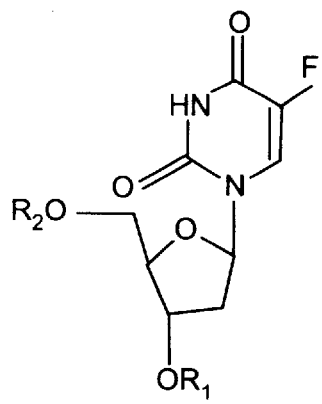
Figure 15E:
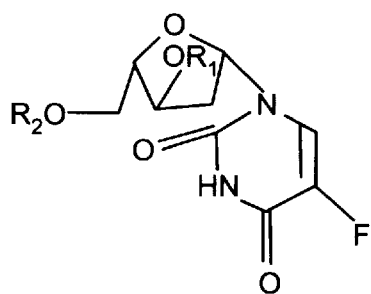
Figure 15E:
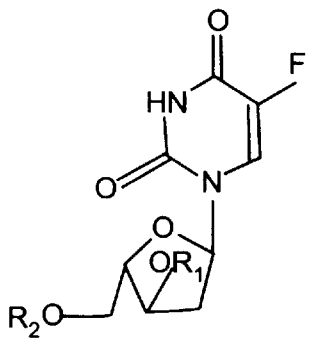
Figure 15E:
Figure 15E:
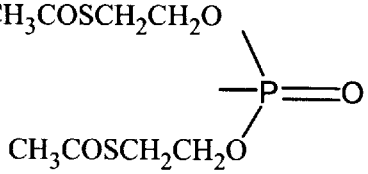

The term "dimers" as used herein is defined by the structures shown in FIG. 1. These compounds are L-nucleoside-derived dinucleoside monophosphates. The $B_1$ and $B_2$ units will consist of either a β-D, a β-L or an α-L nucleoside and at least one of $B_1$ or $B_2$ will be β-L or α-L. $R_1$ and $R_2$ will be the pyrimidine bases cytosine, thymine, uracil, or 5-fluorouridine (5-FUdR) other 5-halo compounds, or the purine bases, adenosine, guanosine or inosine. As can be seen in FIG. 1, the dimers can be bound by various linkages. Permissible linkages include 5'→3', 3'→5', 3'→3', 5'→5', 2'→3', 3'→2', 2'→2', 2'→5', 5'→2', or any other stereochemically permissible linkage. The sugar part of the nucleoside may be fully oxygenated, or may be in the deoxy or dideoxy form.

Specific antidisease compounds which are useful in the present invention include 3'-O-(α-L-5-fluoro-2'-deoxyuridinyl)-β-D-5-fluoro-2'-deoxyuridine, (L-102), 3'-O-(β-D-5-fluoro-2'-deoxyuridinyl)-α-L-5-fluoro-2'-deoxyuridine, (L-103), 3'-O-(β-D-5-fluoro-2'-deoxyuridinyl)-α-L-2'-deoxyuridine, (L-107), 3'-O-(α-L-5-fluoro-2'-deoxyuridinyl)-α-L-5-fluoro-2'-deoxyuridine, (L-108), 3'-O-(β-L-5-fluoro-2'-deoxyuridinyl)-β-L-5-fluoro-2'-deoxyuridine, (L-109), 3'-O-(β-D-5-fluoro-2'-deoxyuridinyl)-β-L-5-fluoro-2'-deoxyuridine, (L-110), 3'-O-(β-D-5-fluoro-2'-deoxyuridinyl)-α-L-2'-deoxycytidine, (L-111), 3'-O-(β-D-5-fluoro-2'-deoxyuridinyl)-2'-deoxy-β-L-cytidine (L-113), 3'-O-(2'-deoxy-β-L-cytidinyl)-3-D-5-fluoro-2'-deoxyuridine (L-114), 3'-O-(2'-deoxy-α-L-cytidinyl)-β-D-5-fluoro-2'-deoxyuridine (L-115), 3'-O-(β-D-5-fluoro-2'-deoxyuridinyl)-β-L-2'-deoxyuridine (L-117), 3'-O-(β-L-5-fluoro-2'-deoxyuridinyl)-α-L-5-fluoro-2'-deoxyuridine (L-1 19), 3'-O-(β-D-5-fluoro-2'-deoxyuridinyl)-α-L-5-fluoro-2'-deoxyuridine (3', 3') (L-122), 3'-O-(3'-deoxy-β-D-adenosinyl)-β-L-2'-deoxyuridine (L-150), 3'-O-(3'-deoxy-β-D-adenosinyl)-β-L-2'-deoxyadenosine (L-151), 3'-O-(3'-deoxy-β-D-adenosinyl)-α-L-2'-deoxyuridine (L-152), 3'-O-(3'-deoxy-β-D-adenosinyl)-β-L-2'-deoxycytidine (L-153), 3'-O-(3'-deoxy-β-D-adenosinyl)-α-L-2'-deoxycytidine (L-154), 3'-O-(3'-deoxy-β-D-adenosinyl)-β-L-2'-deoxyadenosine (L-155), 3'-O-(2'-deoxy-β-D-adenosinyl)-β-L-2'-deoxyadenosine (L-210). In the currently preferred embodiment, 3'-O-(β-D-5-fluoro-2'-deoxyuridinyl)-α-L-5-fluoro-2'-deoxyuridine, (L-103) is used.

The term "internucleotide binding agent" or "IBA" means the backbone binding which links the nucleosides together. Although one skilled in the art will readily recognize a variety of other backbones are available and useful in the present invention. For example, see FIG. 1, where methoxy phosphotriesters, methylphosphonates, phosphorodithioates, phosphorothioates, silyl ethers, sulphonates and ethylenedioxy ethers are shown. Although shown schematically 3'-5' the IBA's can be used to link the sugars 5'→3', 3'→5', 3'→3', 5'→5', 2'→3', 3'→2', 2'→2', 2'→5', 5'→2', or any other stereochemically permissible linkages. In the preferred embodiment, the IBA of the compounds is either phosphodiester or phosphorothioate. The term "antidisease" as used herein refers to any of the activities of the compounds of the present invention to affect a disease state, including antitumor, antineoplastic, anticancer, antiparasitic and antiviral activity.

A compound or composition is said to be "pharmacologically acceptable" if its administration can be tolerated by a recipient mammal. Such an agent is said to be administered in a "therapeutically effective amount" if the amount administered is physiologically significant. An agent is physiologically significant if its presence results in technical change in the physiology of a recipient mammal. For example, in the treatment of cancer or neoplastic disease, a compound which inhibits the tumor growth or decreases the size of the tumor would be therapeutically effective; whereas in the treatment of a viral disease, an agent which slows the progression of the disease or completely treats the disease, would be considered therapeutically effective.

Dosage and Formulation

The antidisease compounds (active ingredients) of this invention can be formulated and administered to inhibit a variety of disease states (including tumors, neoplasty, cancer, bacterial, fungal, parasitic and viral diseases) by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosages given as examples herein are the dosages usually used in treating tumors, neoplasty and cancer. Dosages for antiparasitic and antiviral applications will, in general, be 10–50% of the dosages for anticancer applications.

The dosage administered will be a therapeutically effective amount of active ingredient and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired. Usually a daily dosage (therapeutic effective amount) of active ingredient can be about 5 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 to about 500 milligrams of active ingredient per unit. In these pharmaceutical compositions, the active ingredient will ordinarily be present in an amount of about 0.05–95% by weight based on the total weight of the composition.

The active ingredient can be administered orally in solid dosage forms such as capsules, tablets and powders, or in liquid dosage forms such as elixirs, syrups, emulsions and suspensions. The active ingredient can also be formulated for administration parenterally by injection, rapid infusion, nasopharyngeal absorption or dermoabsorption. The agent may be administered intramuscularly, intravenously, or as a suppository.

Gelatin capsules contain the active ingredient and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium EDTA. In addition, parenteral solutions can contain preservatives such as benzalkonium chloride, methyl- or propyl-paraben and chlorobutanol. Suitable pharmaceutical carriers are described in *Remington's Pharmaceutical Sciences*, a standard reference text in this field.

Additionally, standard pharmaceutical methods can be employed to control the duration of action. These are well known in the art and include control release preparations and can include appropriate macromolecules, for example polymers, polyesters, polyaminoacids, polyvinyl, pyrolidone, ethylenevinylacetate, methyl cellulose, carboxymethyl cellulose or protamine sulfate. The concentration of macromolecules as well as the methods of incorporation can be adjusted in order to control release.

Additionally, the agent can be incorporated into particles of polymeric materials such as polyesters, polyaminoacids, hydrogels, poly (lactic acid) or ethylenevinylacetate copolymers. In addition to being incorporated, these agents can also be used to trap the compound in microcapsules.

Useful pharmaceutical dosage forms for administration of the compounds of this invention can be illustrated as follows.

Capsules:

Capsules are prepared by filling standard two-piece hard gelatin capsulates each with 100 milligram of powdered active ingredient, 175 milligrams of lactose, 24 milligrams of talc and 6 milligrams magnesium stearate.

Soft Gelatin Capsules:

A mixture of active ingredient in soybean oil is prepared and injected by means of a positive displacement pump into gelatin to form soft gelatin capsules containing 100 milligrams of the active ingredient. The capsules are then washed and dried.

Tablets: Tablets are prepared by conventional procedures so that the dosage unit is 100 milligrams of active ingredient. 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

Injectable:

A parenteral composition suitable for administration by injection is prepared by stirring 1.5% by weight of active ingredients in 10% by volume propylene glycol and water. The solution is made isotonic with sodium chloride and sterilized.

Suspension:

An aqueous suspension is prepared for oral administration so that each 5 millimeters contain 100 milligrams of finely divided active ingredient, 200 milligrams of sodium carboxymethyl cellulose, 5 milligrams of sodium benzoate, 1.0 grams of sorbitol solution U.S.P. and 0.025 millimeters of vanillin.

SUMMARY OF COMPOUNDS SYNTHESIZED

The following examples are offered by way of illustration and are not intended to limit the invention in any manner. The nucleosides and dimers may incorporate any stereochemcially permissible linkage na may include various deoxy forms of the sugar rings. The synthetic nucleosides and dimers described in the examples can include any of the substitutions discussed earlier. The backbone and base modifying groups can be added. Various substitutions will enhance the affinity, the chemical stability and the cellular uptake properties of the specific dimers treatments.

EXAMPLE I

Synthesis of 2'-deoxy-α-L-5-flourouridine

While β-D-5-fluoro-deoxyuridine is commercially available, the α-L-isomer 2'-deoxy-α-L-5-fluorouridine is not, and this component of the dimers was synthesized from L-arabinose.

1-(2', 3', 5'-tri-O-benzoyl-α-L-arabinofuranosyl)-5-fluorouracil (3)

To a mixture of 5-fluorouracil (4.01 g, 30.87 mmol) and compound 2 (15.57 g, 30.87 mmol) in anhydrous MeCN were successively added HMDS (5.20 ml, 24.69 mmol), ClSiMe$_3$ (3.10 ml, 24.69 mmol), and SnCl$_4$ (4.30 ml, 37.04 mmol). The resulting clear solution was refluxed for one hour. Then the solvent was evaporated and the residue was dissolved in EtOAc (750 ml), washed with $H_2O$, and saturated $NaHCO_3$ solution. The EtOAc layer was dried over sodium sulfate, filtered and evaporated to give the crude product. This crude product was purified on a silica gel column using 40–50% EtOAc/petroleum ether to give pure 3 (11.7 g, 66.0% yield) as a white foam.

NMR: ($CDCl_3$) δ=4.65 (dd, 1H), 4.78 (dd, 1H), 4.97 (dd, 1H. 5.75–5.88 (2 t, 2H), 6.27 (d, 1H), 7.36–7.62 and 8.00–8.10 (m, 5H), 8.94 (d, 1H).

1-α-L-arabinofuranosyl-5-fluorouracil (4)

To a solution of compound 3 (11.7 g, 20.37 mmol) in MeOH (300 ml), NaOMe (4.2 ml of a methanolic 25% w/v solution) was added and the solution was stirred until the reaction was complete. The solvent was then evaporated and the residue was dissolved in $H_2O$ (200 ml), washed with ether and neutralized with Dowex 50 ion exchange resin. After filtration of the resin, the aqueous solution was evaporated to give compound 4 (4.92 g, 92% yield) as a white foam.

NMR: ($DMSO-d_6$) δ=3.48 (m, 2H), 3.934.00 (2 t, 2H), 4.16 (q, 1H), 5.69 (dd, 1H), 8.03 (d, 1H).

1-[3',5'-O-(1,1,3,3-tetraisopropyldisiloxane-1,3-diyl)-α-L-arabinofuranosyl]-5-fluorouracil (5)

To a stirred suspension of 4 (6.43 g, 24.52 mmol) in pyridine (200 ml) was added 1,3-dichloro-1,1,3,3-tetraisopropyldisiloxane (10.3 ml, 29.43 mmol). This was stirred at room temperature until the reaction was complete (5 hours). The solvent was evaporated to a residue which was dissolved in EtOAC and washed successively with $H_2O$, 5% HCl, $H_2O$, saturated $NaHCO_3$, and brine. After drying the EtOAc portion over $Na_2SO_4$, the solution was filtered and evaporated to give the crude product 5 which was used in the next step without further purification.

1-[2'-O-phenoxythiocarbonyl-3',5'-O-(1,1,3,3-tetraisopropyldisiloxane-1,3-diyl)-α-L-arabinofuraosyl]-5-fluorouracil (6)

To a solution of 5 (24.52 mmol) in anhydrous MeCN (300 ml) were added 4-dimethylaminopyridine (DMAP) (5.80 g, 47.58 mmol), and phenylchlorothionoformate (3.85 ml, 26.98 mmol). The solution was stirred at room temperature for 24 hours. Then, the solvent was evaporated to a residue which was dissolved in EtOAc and washed successively with $H_2O$, 5% HCl, $H_2O$, saturated $NaHCO_3$, and brine. After drying the EtOAc portion over $Na_2SO_4$, the solution was filtered and evaporated to an oil. The oil was purified on a silica gel column using 30% EtOAc/petroleum ether to produce pure 6 (8.9 g, 56.7% yield) as a yellow foam.

NMR: ($CDCl_3$) δ=4.02 (m, 2H), 4.32 (m, 1H), 4.76 (dd, 1H), 6.10 (dd, 1H), 6.18 (dd, 1H), 7.07–7.48 (m, 6H), 8.41 (br s, 1H).

3',5'-O-(1,1,3,3-tetraisopropyldisiloxane-1,3-diyl)-α-L-2'-deoxy-5-fluorouridine (7)

To a solution of 6 (8.92 g, 13.91 mmol), in dry toluene (300 ml) was added AIBN (0.46 g, 2.78 mmol) followed by $Bu_3SnH$ (20.0 ml, 69.35 mmol). The solution was deoxygenated with argon and heated at 75° C. for four hours. The solvent was then evaporated and the residue was purified on a silica gel column using 30% EtOAc/petroleum ether to give pure 7 (5.44 g, 80% yield) as a white foam.

NMR: ($CDCl_3$) δ=2.16 (m, 1H), 2.84 (m, 1H), 3.8 Cm, 1H), 4.07 (m, 1H), 4.60 (m, 1H), 6.19 (ddd, 1H), 7.92 (m, 1H).

2'-deoxy-α-L-5-fluorouridine (8)

A solution of compound 7 (5.44 g, 11.13 mmol) and $NH_4F$ (4.12 g, 111.3 mmol) in MeOH was stirred in an oil bath at 60° C. for 3 hours. Silica gel (3 g) was added and the mixture was evaporated to a dry powder. This powder was added to a silica column and eluted with 10–15% $MeOH/CHCl_3$ to produce pure 8 (2.4 g, 87.6% yield) as a white foam.

NMR: ($DMSO-d_6$) δ=1.90 (m, 1H), 2.55 (m, 1H), 3.33 (m,2H), 4.19 (m, 2H), 4.86(brs, 1H), 5.43(brs, 1H),6.10(dd, 1H), 8.15(d, 1H), 11.78(brs, 1H).

Example 2

Synthesis of 2'-deoxy-α-L-uridine 1-(2', 3', 5'-tri-O-benzovl-α-L-arabinofuranosyl) uracil (9)

To a mixture of uracil (1.17 g, 10.49 mmol) and compound 2 (5 g) in anhydrous MeCN (100 ml) were successively added HMDS (1.77 ml, 8.39 mmol), $ClSiMe_3$ (1.06 ml, 8.39 mmol), and $SnCl_4$ (1.47 ml, 12.58 mmol). The resulting clear solution was refluxed for one hour. Then the solvent was evaporated and the residue was dissolved in EtOAc (200 ml), washed with $H_2O$, and saturated $NaHCO_3$ solution. The EtOAc layer was dried over sodium sulfate, filtered and evaporated to give the crude product, which was purified on a silica gel column using 40–50% EtOAc/petroleum ether to give pure 9 (3.66 g, 62.7% yield) as a white foam.

NMR: ($CDCl_3$) δ=4.70 (m, 1H), 5.77 (5, 1H), 5.80 (dd, 1H), 5.94 (t, 1H), 6.20 (d, 1H), 7.40–8.10 (m, 16H), 8.58 (br s, 1H).

1-α-L-arabinofuranosyl-uracil (10)

To a solution of compound 8 (17.83 g, 32.03 mmol) in MeOH (400 ml), NaOMe (5.0 ml of a methanolic 25% w/v solution) was added and the solution was stirred until the reaction was complete. The solvent was then evaporated and the residue was dissolved in $H_2O$ (250 ml), washed with ether and neutralized with Dowex 50 ion exchange resin. After filtration of the resin, the aqueous solution was evaporated to give compound 10 (7.4 g, 94.6% yield) as a white foam. This was used in the next step without further purification.

1-[3',5'-o-(1,1,3,3-tetraisopropyldisiloxane-1,3-diyl)-α-L-arabinofuranosyl]-uracil (11)

To a stirred suspension of 10 (7.4 g, 30.3 mmol) in pyridine was added 1.3-dichloro-1,1,3,3-tetraisopropyldisiloxane (12.74 ml, 36.36 mmol). This was stirred at room temperature until the reaction was complete (5 hours). The solvent was evaporated to a residue which was dissolved in EtOAC (500 ml) and washed successively with $H_2O$, 5% HCl, $H_2O$, saturated $NaHCO_3$, and brine. After drying the EtOAc portion over $Na_2SO_4$, the solution was filtered and evaporated to give the crude product 11 which was used in the next step without further purification.

1-[2'-o-phenoxythiocarbonyl-3',5'-o-(1,1,3,3-tetraisopropyldisiloxane-1,3-diyl)-α-L-arabinofuranosyl]-uracil (12)

To a solution of 11 (30.3 mmol) in anhydrous MeCN were added 4-dimethylaminopyridine (DMAP) (7.2 g, 58.78 mmol), and phenylchlorothionoformate (4.7 ml, 33.33 mmol). The solution was stirred at room temperature for 24 hours. Then, the solvent was evaporated to a residue which was dissolved in EtOAc (750 ml) and washed successively with $H_2O$, 5% HCl, $H_2O$, saturated $NaHCO_3$, and brine. After drying the EtOAc portion over $Na_2SO_4$, the solution was filtered and evaporated to an oil. The oil was purified on a silica gel column using 30% EtOAc/petroleum ether to produce pure 12 (13.14 g, 74.5% yield) as a white foam.

NMR: ($CDCl_3$) δ=4.04 (m, 2H), 4.38 (m, 1H), 4.73 (dd, 1H), 5.79 (dd, 1H), 5.93 (d, 1H), 6.31 (dd, 1H), 7.08–7.33 (m, 6H), 9.2 (br s, 1H).

3',5'-o-(1,1,3,3-tetraisopropyldisiloxane-1.3-diyl)-α-L-2'-deoxyuridine (13)

To a mixture of 12 (13.14 g, 21.09 mmol), in dry toluene (300 ml) was added AIBN (0.69 g, 4.2 mmol) followed by Bu$_3$SnH (28.4 ml, 105.4 mmol). The solution was deoxygenated with argon and heated at 75° C. for four hours. The solvent was then evaporated and the residue was purified on a silica gel column using 30% EtOAc/petroleum ether to give pure 13 (9.29 g, 88.4% yield) as a white foam.

NMR: (CDCl$_3$) δ=2.15 (2 t, 1H), 2.81 (m, 1H), 3.82 (dd, 1H), 4.05 (m, 2H), 4.56 (q, 1H), 5.75 (dd, 1H), 6.16 (t, 1H), 7.69 (d, 1H), 9.38 (br s, 1H).

2'-deoxy-α-L-uridine (14)

A mixture of compound 13(9.2 g, 18.63 mmol) and NH$_4$F (6.9 g, 186.3 mmol) in MeOH (200 ml) was stirred in an oil bath at 60° C. for 3 hours. Silica gel (5 g.) was added and the mixture was evaporated to a dry powder. This powder was added to a silica column and eluted with 10–15% MeOH/CHCl$_3$ to produce pure 14 (3.70 g, 83% yield) as a white foam.

NMR: (DMSO-d$_6$) δ=1.87 (m, 1H), 2.56 (m, 1H), 3.41 (m, 2H), 4.15 (m, 1H), 4.22 (m, 1H), 4.44 (t, 1H), 4.92 (t, 1H), 5.38 (d, 1H), 5.62 (d, 1H), 6.09 (dd, 1H).

EXAMPLE 3

Synthesis of 2'-deoxy-α-L-cytidine

3',5'-di-O-benzoyl-2'-deoxy-α-L-uridine (15)

A solution of BzCN (0.61 g, 4.67 mmol) in MeCN (10 ml) was added dropwise to a suspension of compound 14 (0.43 g, 1.87 mmol) in MeCN (10 ml) followed by Et$_3$N (0.1 ml). The reaction was stirred at room temperature for three hours after which time the solvent was evaporated to dryness. The crude material was purified on a silica gel column using 50% EtOAc/petroleum ether to give pure 15 (0.57 g, 70% yield) as yellow foam.

NMR: (CDCl$_3$) δ=2.55 (d, 1H), 2.96 (dt, 1H), 4.56 (m, 2H), 4.86 (t, 1H), 5.61 (d, 1H), 5.73 (dd, 1H), 6.31 (dd, 1H), 7.40–7.63 (m, 7H), 7.87–8.06 (m, 4H), 8.82 (br s, 1H).

3',5'-di-O-benzoyl-2'-deoxy-4-thio-α-L-uridine (16)

A boiling solution of compound 15 (0.54 g, 1.25 mmol) in anhydrous dioxane was treated with P$_2$S$_5$ (0.61 g, 2.75 mmol) and the mixture was refluxed under a nitrogen atmosphere for one hour. Remaining solids were filtered from the hot solution and washed on the filter with additional dioxane. The filtrate was evaporated to dryness and the crude product was purified on a silica gel column using 30% EtOAc/petroleum ether to give pure 16 (0.42 9, 74% yield) as a yellow oil.

NMR: (CDCl$_3$) δ=2.59 (d, 1H), 2.93 (dt, 1H), 4.58 (m, 2H), 4.89 (t, 1H), 5.63 is (d, 1H), 6.26 (dd, 1H), 6.41 (dd, 1H), 7.40–8.10 (m, 11H), 9.54 (brs, 1H).

2'-deoxy-α-L-cytidine (17)

Compound 16 (0.42 g, 9.28 mmol) was treated with NH$_3$/MeOH (50 ml) in a steel bomb at 100° C. for 10 hours. After cooling, the solvent was evaporated to dryness, the residue was dissolved in water (50 ml) and washed with ether (3×50 ml). The water layer was treated with charcoal, filtered through Celite and evaporated to dryness by coevaporation with EtOH. The semi-solid obtained was crystallized from EtOH/ether to give compound 17 (0.18 g, 85.7% yield).

NMR: (DMSO-d$_6$) δ=1.86 (Cd,H), 2.50 (m, 1H), 3.40 (m, 1H), 4.12 (m, 1H), 4.15 (m, 1H), 4.86 (t, 1H), 5.21 (d, 1H), 5.69 (d, 1H), 6.03 (dd, 1H), 7.02 (br d, 1H), 7.74 (d, 1H).

N$^4$-benzoyl-2'-deoxy-α-L-cytidine (18)

ClSiMe$_3$ (2.3 ml, 18.05 mmol) was added dropwise over 30 minutes to a stirring suspension of compound 17 (0.82 g, 3.61 mmol) in pyridine (50 ml) chilled in an ice bath. BzCl (2.1 ml, 18.05 mmol) was then added dropwise and the reaction mixture was cooled at room temperature for two hours. The reaction mixture was again cooled in an ice bath and cold water (10 ml) was added dropwise. Fifteen minutes later, concentrated NH$_4$OH (10 ml) was added to produce a solution of ammonia of a concentration of about 2M. Thirty minutes after the addition of the ammonia solution, a solvent was evaporated, dissolved in water and washed with ether. Evaporation of this aqueous solution provided the crude product (18) which was used in the next step without further purification.

EXAMPLE 4

Synthesis of Dimers

The dimers were prepared from the monomeric materials by the general scheme shown in Scheme 2.

A. α-L, β-D 5 FUdR Dimer

5'-O-dimethoxvtrityl-α-L-5-fluoro-2'-deoxyuridine (20a)

α-L-5-fluoro-2'-deoxyuridine (8) (500 mg, 2.0 mmol) was dissolved in 10 ml of dry, distilled pyridine. To this solution was added 4,4'-dimethoxytrityl chloride (813 mg, 2.4 mmol) and 4-dimethylaminopyridine (DMAP) (50 mg, 0.4 mmol). The mixture was stirred under an argon atmosphere for 16 hours. After this time, the pyridine was stripped off in vacua. The residue was dissolved in EtOAc (50 ml). The organic layer was washed with saturated NaHCO$_3$, water and with brine. The organic layer was dried over Na$_2$SO$_4$, filtered and evaporated in vacuo to a residue which was purified on a silica gel column using 10% MeOH/CHCl$_3$. Pure fractions were pooled and evaporated to give the pure product as an off-white foam (679 mg, 86% yield). Rf=0.48 in 10% MeOH/CHCl$_3$.

NMR: (DMSO-d$_6$) δ=2.3 (dd, 1H), 2.72–2.81 (m, 1H), 3.15–3.26 (m, 2H), 3.75 (s, 6H), 4.45 (m, 2H), 6.23 (dd, 1H), 6.92 (d, 1H), 7.2–7.3 (m, 13 H), 7.94 (d, 1H).

5'-O-dimethoxvtrityl-α-L-5-fluoro-2'-deoxyuridine-3'-N,N-diisopropylmethoxy phosphoramidite (21a)

The 5'-O-dimethoxytrityl-α-L-5-fluoro-2'-deoxyuridine (20a, 548 mg, 1 mmol) was dissolved in anhydrous dichloromethane (20 ml). N,N-diisopropylethylamine (700 pi, 4 mmol) was added through a septum, followed by chloro-N,N-diisopropylmethoxyphosphine (290 pi, 1.5 mmol), under an argon atmosphere. The reaction was stirred for 30 minutes. The solvent was evaporated and the residue was partitioned between an 80% EtOAc/triethylamine mixture and brine. The organic layer was washed with saturated NaHCO$_3$ solution and brine. The organic residue was evaporated to dryness and the residue was purified on a silica gel column using a mixture of dichloromethane, EtOAc and triethylamine (45:45:10;Rf=0.69). The product (390 mg) was isolated as a yellow foam and it was used in the next step without further purification.

3'-Acetoxy-β-D-5-fluoro-2'-deoxyuridine (24a)

β-D-5-fluoro-2'-deoxyuridine (500 mg, 2.2 mmol) was dissolved in 10 20 ml of dry, distilled pyridine. To this solution was added 4,4'-dimethoxytrityl chloride (813 mg, 2.4 mmole) and 4-dimethylaminopyridine (DMAP) (50 mg, 0.4 mmole). The mixture was stirred at room temperature for 16 hours. The pyridine was stripped off in vacuo. The residue was dissolved in dichloromethane (50 ml). The organic layer was washed with 0.3 NHCl, brine, saturated NaHCO$_3$, and again with brine. The organic layer was dried over Na$_2$SO$_4$, filtered and evaporated in vacuo to a residue which was purified on a silica gel column, eluting with 10% MeOH/CHCl$_3$. Pure fractions were pooled and evaporated to give the pure product as an off-white foam (685 mg, 86% yield). This material was dissolved in pyridine (12 ml) and treated with acetic anhydride (2.5 ml) for 3 hours at room temperature. The solvent was evaporated, and the residue was dissolved in ethyl acetate. The ethyl acetate was washed as described above, dried over sodium sulfate and evaporated. The residue was then treated with 80% acetic acid (10 ml) for 2.5 hours at room temperature. The solvent was evaporated in vacuo and the residue was chromatographed on silica gel, eluting with 10% MeOH/CHCl$_3$ to give pure 24a as a white foam, yield 422 mg.

NMR: (DMSO-d$_6$) δ=1.95 (s, 3H), 2.08–2.24 (m, 2H), 3.65–3.9 (m, 2H), 4.45 10 (m, 1H), 4.72 (m, 1H), 6.24 (dd, 1H), 8.24 (d, 1H).

5'-O-dimethoxytrityl-3'-[O-(3'-O-acetyl)-β-D-5-fluoro-2'-deoxyuridinyl]-α-L-5-fluoro-2'-deoxyuridine (25a)

The 3'-O-acetyl-β-D-5-fluoro-2'-deoxyuridine (188 mg, 0.65 mmol) was dissolved in dry acetonitrile (5 ml). Sublimed 1H-tetrazole (80 mg) was added and the mixture was stirred under an argon atmosphere for 15 minutes. The solution of 21a (380 mg, 0.54 mmol), dissolved in 5 ml of dry acetonitrile was added via syringe to the reaction solution over 5 minutes.

The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (468 mg). This foam was used in the next step without further purification.

(3'-acetoxy-β-D-5-fluoro-2'-deoxyuridinyl)-α-L-5-fluoro-2'-deoxyuridine methyl phosphonate ester (26a)

The dimer, 25a (504 mg), was dissolved in 8 ml of THF and 2 ml of pyridine containing 0.2 ml of water. Iodine crystals (26 mg) were added and the contents of the loosely stoppered flask were allowed to stir for 2.1 hours. Excess iodine was discharged by the addition of a few drops of saturated sodium thiosulfate. The reaction mixture was then evaporated to dryness.

The crude product was dissolved in EtOAc washed with saturated NaHCO$_3$ solution and brine. The organic layer was dried over Na$_2$SO$_4$, filtered and evaporated in vacuo. The residue (530 mg) was dissolved in 10 ml of 80% acetic acid/water solution and was stirred until the reaction was completed. The solvent was evaporated and the residue was purified on a silica gel column, using 20% MeOH/CHCl$_3$. Fractions containing one spot by TLC (10% MeOH/CHCl$_3$ Rf=0.35) were pooled and evaporated to give the pure product (316 mg).

NMR: (CD$_3$OD) δ=2.08 (s, 3H), 2.25–2.45 (m, 3H), 2.65–2.72 (m, 1H), 3.60 (m, 2H), 3.80 (2d, 3H), 4.18 (m, 1H), 4.28 (m, 1H), 4.35 (dd, 1H), 4.62 (dd, 1H), 5.05 (dd, 1H), 5.23 (m, 1H), 6.13 (m, 1H), 6.18 (m, 1H), 7.85 (m, 2H).

P$^{31}$NMR: (CD$_3$OD) δ=0.77 (s), 1.16 (s).

3'-O-(β-D-5-fluoro-2'-deoxyuridinyl)-α-L-5-fluoro-2'-deoxyuridine (27a)

The O-protected dimer, 26a (280 mg) was treated with 20 ml of saturated methanolic ammonia at room temperature until the reaction was completed at room temperature. The solvent was stripped off in vacuo and the residue was purified on DEAE cellulose ion exchange column using gradient of NH$_4$CO$_3$ buffer from 0.02–0.2M. Pure fractions were evaporated at 40° C. in high vacuo to dryness to give the pure product (162 mg).

NMR: (D$_2$O) δ=2.2–2.4 (m, 3H), 2.65–2.71 (m, 1H), 3.65 (m, 2H), 4.01 (m, 1H), 4.11 (t, 1H), 4.45 (m, 1H), 4.65 (t, 1H), 6.14 (d, 1H), 6.24 (td, 1H), 8.06 (d, 1H), 8.02 (d, 1H).

$^{31}$P NMR: (D$_2$O) δ=0.04 (s).

B. β-D, α-L 5FUdR Dimer

5'-O-dimethoxytrityl-3'-[O-(3'-O-acetyl)-α-L-5-fluoro-2'-deoxguridinyl]-β-D-5-fluoro-2'-deoxyuridine (25b)

The 3'-O-acetyl-α-L-5-fluoro-2'-deoxyuridine, 24b (188 mg, 0.65 mmol) was dissolved in dry acetonitrile (5 ml). Sublimed 1H-tetrazole (80 mg) was added and the mixture was stirred under an argon atmosphere for 15 minutes. The solution of 21b (380 mg, 0.54 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (484 mg). This foam was used in the next step without further purification.

(3'-acetoxy-α-L-5-fluoro-2'-deoxyuridinyl)-β-D-5-fluoro-2'-deoxyuridine methyl phosphate ester (26b)

The dimer, 25b (526 mg), was dissolved in 8 ml of THF and 2 ml of pyridine containing 0.2 ml of water. Iodine crystals (26 mg) were added and the contents of the loosely stoppered flask were allowed to stir for 1 hour. Excess iodine was discharged by the addition of a few drops of saturated sodium thiosulfate. The reaction mixture was then evaporated to dryness. The crude product was dissolved in EtOAc washed with saturated NaHCO$_3$ solution and brine. The organic layer was dried over Na$_2$SO$_4$, filtered and evaporated in vacuo. The residue (578 mg) was dissolved in 10 ml of 80% acetic acid/water solution and was stirred for three hours. The solvent was evaporated and the residue was purified on a silica gel column, using 10–15% MeOH/CHCl$_3$. Fractions containing one spot by TLC (10% MeOH/CHCl$_3$ Rf=0.35) were pooled and evaporated to give the pure product (342 mg).

NMR: (DMSO-d$_6$) δ=1.98 (s, 3H), 2.2–2.4 (m, 3H), 2.62–2.71 (m, 1H), 3.5–3.8(m,4H), 4.02(m, 1H),4.42(m, 2H),6.10(dd, 1H), 6.26(dt, 1H), 8.00 (d, 1H), 8.04 (d, 1H).

3'-O-(α-L-5-fluoro-2'-deoxyuridinyl)-β-D-5-fluoro-2'-deoxyuridine (27b)

The O-protected dimer, 26b (170 mg) was treated with 20 ml of saturated methanolic ammonia at room temperature until the reaction was completed. The solvent was stripped off in vacuo and the residue was purified on DEAE cellulose ion exchange column using gradient of NH$_4$CO$_3$ buffer from 0.02–0.2M. Pure fractions were evaporated at 40° C. in high vacuo to dryness to give the pure product (89 mg).

NMR: (D$_2$O) δ=2.2–2.4 (m, 3H), 2.65–2.71 (m, 1H), 3.54–3.85 (m, 5H), 4.05 (t, 1H), 4.42 (m, 2H), 6.06 (dd, 1H), 6.23 (dt, 1H), 8.00 (d, 1H), 8.04 (d, 1H).

C. α-L uridine, β-D 5 FUdR dimer 5'-O-(di-p-methoxytrityl)-2'-deoxy-α-L-uridine (20c)

α-L-2'-deoxyuridine (1.5 g, 6.57 mmol) was dissolved in 25 ml of dry, distilled pyridine. To this solution was added 4,4'-dimethoxytrityl chloride (2.9 g, 7.89 mmol) and 4-dimethylamino pyridine (DMAP) (160 mg, 1.31 mmol). The mixture was stirred under an argon atmosphere for 16 hours. After this time, the pyridine was stripped off in vacuo. The residue was dissolved in EtOAc (150 ml). The organic layer was washed with saturated NaHCO$_3$, water and again with brine. The organic layer was dried over Na$_2$SO$_4$, filtered and evaporated in vacuo to a residue which was purified on a silica gel column using 5% MeOH/CHCl$_3$. Pure fractions were pooled and evaporated to give the pure product as an off-white foam (2.84 g, 81% yield).

NMR: (CDCl$_3$-d$_6$) δ=2.29 (d, 1H), 2.70 (m, 2H), 3.17 (m, 2H), 3.78 (s, 6H), 4.44 (m, 2H), 5.63 (d, 1H), 6.19 (d, 1H), 6.83 (d, 4H), 7.28 (m, 9 H), 7.68 (d, 1H), 9.30 (br s, 1H).
5'-O-(dimethoxytrityl)-α-L-2'-deoxyuridine-3'-N,N-diisopropylmethoxy phosphoramidite (21c).

The 5'-O-dimethoxytrityl-α-L-2'-deoxyuridine (2.35 g, 4.43 mmol) was dissolved in anhydrous dichloromethane (50 ml). N,N-diisopropylethylamine (3.1 ml, 17.72 mmol) was added through a septum, followed by chloro-N,N-diisopropylmethoxyphosphine (1.3 ml, 6.64 mmol), under an argon atmosphere. The reaction was stirred for 30 minutes. The solvent was evaporated and the residue was partitioned between an 80% EtOAc/triethylamine mixture and brine. The organic layer was washed with saturated NaHCO$_3$ solution and brine. The organic residue was evaporated to dryness and the residue was purified on a silica gel column using a 5 mixture of dichloromethane, EtOAc and triethylamine (40:50:10; Rf=0.69). The product was isolated quantitatively as a yellow foam and it was used in the next step without further purification.

5 '-O-dimethoxytrityl-3'-[O-(3'-O-acetyl)-β-D-5-fluoro-2'-deoxyuridinyl]-2'-deoxy-α-L-uridine (25c)

The 3'-O-acetyl-β-D-5-fluoro-2'-deoxyuridine (0.95 g, 3.29 mmol) was dissolved in dry acetonitrile (125 ml). Sublimed 1H-tetrazole (350 mg, 4.91) was added and the mixture was stirred under an argon atmosphere for 15 minutes. The solution of 21c (4.91 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam. This compound was further purified on a silica gel column using 5% MeOH/CHCl$_3$ to give the pure product (2.81 g, 97% yield).

3'-acetoxy-β-D-5'-fluoro-2'-deoxyuridinyl)-α-L-2'-deoxyuridine methyl phosphate ester (26c)

The dimer, 25c (2.81 g, 3.2 mmol), was dissolved in a mixture of THF:pyridine:water (25:6:0.6). Iodine crystals (150 mg) were added and the contents of the loosely stoppered flask were allowed to stir for 1 hour. Excess iodine was discharged by the addition of a few drops of saturated sodium thiosulfate. The reaction mixture was then evaporated to dryness. The crude product was dissolved in EtOAc washed with saturated NaHCO$_3$ solution and brine. The organic layer was dried over Na$_2$SO$_4$, filtered and evaporated in vacuo. The residue (1.48 g) was dissolved in 25 ml of 80% acetic acid/water solution and was stirred until the reaction was completed. The solvent was evaporated and the residue was purified on a silica gel column, using 10% MeOH/CHCl$_3$. Fractions containing one spot by TLC (10% MeOH/CHCl$_3$ Rf=0.4) were pooled and evaporated to give the pure product (0.465 g, 25% yield).

NMR: (CD$_3$OD) δ=2.09 (d, 3H), 2.40 (m, 3H), 2.80 (m, 1H), 3.78 (dd, 3H), 4.30 (m, 3H), 4.63 (m, 1H), 5.05 (m, 1H), 5.23 (m, 1H), 5.70 (d, 1H), 6.13 (m, 1H), 6.20 (m, 1H), 7.73 (d, 1H), 7.82 (d, 1H).

P$^{31}$NMR: (CD$_3$OD) δ=0.56 (s), 0.84 (s).

3'-O-(β-D-5-fluoro-2'-deoxyuridinyl)-α-L-2'-deoxyuridine (27c)

The O-protected dimer, 26c (465 mg, 0.78 mmol) was treated with 50 ml of saturated methanolic ammonia at room temperature until the reaction was completed. The solvent was stripped off in vacuo and the residue was purified on DEAE cellulose ion exchange column using gradient of NH$_4$CO$_3$ buffer from 0.02–0.2M. Pure fractions were evaporated at 40° C. in high vacuo to dryness to give the pure product (370 mg, 87.7% yield).

N NMR: (CD$_3$OD) δ=2.23 (m, 2H), 2.29 (d, 1H), 2.73(m, 1H), 4.0 (d, 2H), 4.42 (m, 1H), 4.56 (m, 1H), 4.81 (m, 1H), 5.69 (d, 1H), 6.24 (m, 2H), 7.85 (d, 1H), 8.02 (d, 1H).

P$^{31}$ NMR: (CD$_3$OD) δ=1.25 (s).

D. β-L. β-L 5 FUdR dimer

5'-O-dimethoxytrityl-β-L-5-fluoro-2'-deoxyuridine (20d)

β-L-5-fluoro-2'-deoxyuridine (19d, 1.42 g, 5.77 mmol) was dissolved in 25 ml of dry, distilled pyridine. To this solution was added 4,4'-dimethoxytrityl chloride (2.34 g, 6.92 mmol) and 4-dimethylamino pyridine (DMAP) (140 mg, 1.15 mmol). The mixture was stirred under an argon atmosphere for 16 hours. After this time, the pyridine was stripped off in vacuo. The residue was dissolved in EtOAc (100 ml). The organic layer was washed with saturated NaHCO$_3$, and with brine. The organic layer was dried over Na$_2$SO$_4$, filtered and evaporated in vacuo to a residue which was purified on a silica gel column using 5% MeOH/CHCl$_3$. Pure fractions were pooled and evaporated to give the pure product as an off-white foam (2.88 g, 88.7% yield).

NMR: (CDCl$_3$) δ=2.25 (m, 1H), 2.50 (m, 1H), 3.50 (m, 2H), 3.80 (s, 6H), 4.08 (m, 1H), 4.58 (m, 1H), 6.30 (t, 1H), 6.84 (d, 4H), 7.28 (m, 9 H), 7.82 (d, 1H), 8.58 (br s, 1H).

5'-O-dimethoxytrityl-β-L-5-fluoro-2'-deoxyuridine-3'-N,N-diisopropylmethoxy phosphoramidite (21d)

The 5'-O-dimethoxytrityl-β-L-5-fluoro-2'-deoxyuridine (20d, 840 mg, 1.53 mmol) was dissolved in anhydrous dichloromethane (50 ml). N,N-diisopropylethylamine (1.1 ml, 6.13 mmol) was added through a septum, followed by chloro-N,N-diisopropylmethoxyphosphine (0.42 ml, 2.3 mmol), under an argon atmosphere. The reaction was stirred for 30 minutes. The solvent was evaporated and the residue was partitioned between an 80% EtOAc/triethylamine mixture and brine. The organic layer was washed with saturated NaHCO$_3$ solution and brine. The organic residue was evaporated to dryness and the residue was purified on a silica gel column using a mixture of dichloromethane, EtOAc and triethylamine (45:45:10; Rf=0.69). The product (700 mg, 65%) was isolated as a yellow foam and it was used in the next step without further purification.

5 '-O-dimethoxytrityl-3'-[O-(3'-O-acetyl)-β-L-5-fluoro-2'-deoxyuridinyl]-β-L-5-fluoro-2'-deoxyuridine (25d)

The 3'-acetyl-β-L-5-deoxyuridine, 24d (330 mg, 1.15 mmol) was dissolved in dry acetonitrile (50 ml). Sublimed 1H-tetrazole (120 mg, 1.77 mmol) was added and the mixture was stirred under an argon atmosphere for 15 minutes. The solution of 21d (950 mg, 1.36 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam.

This foam was purified on a silica gel column using 5% MeOH/CHCl$_3$ to give the pure product (960 mg, 93% yield).

NMR: (CDCl$_3$) δ=2.10 (d, 3H), 2.28 (m, 2H), 2.49 (m, 2H), 3.42 (m, 3H), 3.51 (dd, 3H), 3.76 (s, 6H), 4.07 (m, 1H), 4.55 (m, 1H), 4.87 (m, 1H), 5.23 (m, 1H), 6.30 (m, 2H), 6.84 (d, 4H), 7.30 (m, 9H), 7.82 (m, 2H).

(3'-acetoxy-β-L-5-fluoro-2'-deoxyuridinyl)-β-L-5-fluoro-2'-deoxyuridine methyl phosphate ester (26d)

The dimer, 25d (960 mg, 1.07 mmol), was dissolved in a mixture containing THF:pyridine:water (12:3:0.3). Iodine crystals (50 mg) were added and the contents of the loosely stoppered flask were allowed to stir for 1 hour. Excess iodine was discharged by the addition of a few drops of saturated sodium thiosulfate. The reaction mixture was then evaporated to dryness. The crude product was dissolved in EtOAc washed with saturated NaHCO$_3$ solution and brine. The organic layer was dried over Na$_2$SO$_4$, filtered and evaporated in vacuo. The residue (530 mg) was dissolved in 20 ml of 80% acetic acid/water solution and was stirred until the reaction was completed. The solvent was evaporated and the residue was purified on a silica gel column, using 10% MeOH/CHCl$_3$. Fractions containing one spot by TLC (10% MeOH/CHCl$_3$ Rf=0.35) were pooled and evaporated to give the pure product (310 mg, 46% yield).

NMR: (CD$_3$OD) δ=2.08 (s, 3H), 2.35–2.54 (m, 4H), 3.79 (m, 2H), 3.83 (dd, 3H), 4.18 (m, 2H), 5.08 (m, 1H), 5.29 (m, 1H), 6.24 (m, 1H), 7.86 (dd, 1H), 8.19 (dd, 1H).

P$^{31}$ NMR: (CD$_3$OD) δ=0.82 (s), 1.03 (s).

3'-O-(β-L-5-fluoro-2'-deoxyuridinyl)-β-L-5-fluoro-2'-deoxyuridine (27d)

The O-protected dimer, 26d (300 mg, 0.49 mmol) was treated with 50 ml of saturated methanolic ammonia at room temperature until the reaction was completed. The solvent was stripped off in vacuo and the residue was purified on DEAE cellulose ion exchange column using gradient of NH$_4$CO$_3$ buffer from 0.02–0.2M. Pure fractions were evaporated at 40° C. in high vacuo to dryness to give the pure product (240 mg, 85% yield). NMR: (CD$_3$OD) δ=2.25 (m, 3H), 2.50 (m, 1H), 3.79 (d, 2H), 4.03 (m, 1H), 4.08 (m, 2H), 4.18 (m, 1H), 4.44 (m, 1H), 4.90 (m, 1H), 6.25 (t, 1H), 8.01 (d, 1H), 8.24 (d, 1H).

P$^{31}$ NMR: (CD$_3$OD) δ=0.18 (s).

E. β-L, β-D 5 FUdR dimer

5'-O-dimethoxytrityl-3'-[O-(3'-O-acetyl)-β-D-5-fluoro-2'-deoxyuridinyl]-(-L-5-fluoro-2'-deoxyuridine (25e)

The 3'-O-acetyl-⊖-D-5-fluoro-2'-deoxyuridine (250 mg, 0.97 mmol) was dissolved in dry acetonitrile (50 ml). Sublimed 1H-tetrazole (100 mg, 1.46 mmol) was added and the mixture was stirred under an argon atmosphere for 15 minutes. The solution of 21e (1.02 g, 1.46 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam. This foam was purified on a silica gel column using 5% MeOH/CHCl$_3$ to give the pure product quantitatively.

(3'-acetoxy-β-D-5-fluoro-2'-deoxyuridinyl)-β-L-5-fluoro-2'-deoxyuridine methyl phosphonate ester (26e)

The dimer in reduced form, 25 (700 mg, 0.78 mmol), was dissolved in a mixture containing THF:pyridine:water (25:6:0.6). Iodine crystals (100 mg) were added and the contents of the loosely stoppered flask were allowed to stir for 2.5 hours. Excess iodine was discharged by the addition of a few drops of saturated sodium thiosulfate. The reaction mixture was then evaporated to dryness. The crude product was dissolved in EtOAc washed with saturated NaHCO$_3$ solution and brine. The organic layer was dried over Na$_2$SO$_4$, filtered and evaporated in vacuo. The residue was dissolved in 25 ml of 80% acetic acid/water solution and was stirred until the reaction was completed. The solvent was evaporated and the residue was purified on a silica gel column, using 10% MeOH/CHCl$_3$. Fractions containing one spot by TLC (10% MeOH/CHCl$_3$ Rf=0.35) were pooled and evaporated to give the pure product (340 mg, 71.4% yield).

NMR: (DMSO-d$_6$) δ=2.06 (s, 3H), 2.37 (m, 4H), 3.45 (m, 2H), 3.65 (d, 3H), 4.20 (m, 3H), 4.95 (m, 1H), 5.30 (m, 1H), 5.96 (m, 1H), 6.15 (t, 2H), 7.99 (d, 1H), 8.16 (d, 1H), 11.90(br s, 2H).

P$^{31}$ NMR: (DMSO-d$_6$) δ=1.93 (s), 2.01 (s).

3'-O-(β-D-5-fluoro-2'-deoxyuridinyl)-3-L-5-fluoro-2'-deoxyuridine (27e)

The O-protected dimer, 26e (340 mg, 0.57 mmol) was treated with 100 ml of saturated methanolic ammonia at room temperature until the reaction was completed. The solvent was stripped off in vacuo and the residue was purified on DEAE cellulose ion exchange column using gradient of NH$_4$CO$_3$ buffer from 0.02–0.2M. Pure fractions were evaporated at 40° C. in high vacuo to dryness to give the pure product (200 mg, 66.9% yield).

NMR: (CD$_3$OD) δ=2.20 (m, 3H), 2.53 (m, 1H), 3.79 (d, 2H), 4.05 (m, 3H), 4.16 (m, 1H), 4.45 (m, 1H), 6.27 (t, 2H), 8.01 (d, 1H), 8.04 (d, 1H), 8.26 (d, 1H).

5'-O-(dimethoxytrityl)-α-L-5-fluoro-2'-deoxyuridine-3'-N N-diisopropylcyanoethyl phosphoramidite (21f)

The 5'-o-dimethoxytrityl-α-L-5-fluoro-2'-deoxyuridine (1.48 g, 2.71 mmol) was dissolved in anhydrous dichloromethane (50 ml). N,N-diisopropylethylamine (1.9 ml, 10.84 mmol) was added through a septum, followed by 2'-cyanoethyl-N,N-diisopropylchlorophosphoramidite (0.78 ml, 3.52 mmol), under an argon atmosphere. The reaction was stirred for 30 minutes. The solvent was evaporated and the residue was partitioned between an 80% EtOAc/triethylamine mixture and brine. The organic layer was washed with saturated NaHCO$_3$ solution and brine. The organic residue was evaporated to dryness and the residue was purified on a silica gel column using a mixture of dichloromethane, EtOAc and triethylamine (45:45:10: Rf=0.7). The product was isolated quantitatively as a yellow foam and it was used in the next step without further purification.

5'-O-dimethoxytrityl-3'-[O-(5'-O-dimethoxytrityl)-β-D-5-fluoro-2'-deoxyuridinyl]-α-L-5-fluoro-2'-deoxyuridine (25f)

The 5'-O-dimethoxytrityl-β-D-5-fluoro-2'-deoxyuridine (0.44 g, 0.81 mmol) was dissolved in dry acetonitrile (20 ml). Sublimed 1H-tetrazole (90 mg) was added and the mixture was stirred under an argon atmosphere for 15 minutes. The solution of 21f (0.51 mg, 0.67 mmol), dissolved in 10 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (970 mg). This foam was used in the next step without further purification.

(β-D-5-fluoro-2'-deoxyuridinyl)-α-L-5-fluoro-2'-deoxyuridine cyanoethyl phosphonate ester (26f)

The dimer, 25f (970 mg), was dissolved in 16 ml of THF and 4 ml of pyridine containing 0.4 ml of water. Iodine crystals (50 mg) were added and the contents of the loosely stoppered flask were allowed to stir for 1 hour.

Excess iodine was discharged by the addition of few drops of saturated sodium thiosulfate. The reaction mixture was then evaporated to dryness.

The crude product was EtOAc washed with saturated NaHCO$_3$ solution and brine. The organic layer was dried over Na$_2$SO$_4$, filtered and evaporated in vacuo. The residue was dissolved in 20 ml of 80% acetic acid/water solution and was stirred until the reaction was completed. The solvent was evaporated and the residue was purified on a silica gel column, using 10–15% MeOH/CHCl$_3$. Fractions containing one spot by TLC (10% MeOH/CHCl$_3$ Rf=0.35) were pooled and evaporated to give the pure product (330 mg).

3'-O-(13-D-5-fluoro-2'-deoxyuridinyl)-α-L-5-fluoro-2'-deoxyuridine (27f)

The O-protected dimer, 26f (200 mg) was treated with 20 ml of concentrated ammonia solution until the reaction is completed. The solvent was stripped off in vacuo and the residue was purified on DEAE cellulose ion exchange column using gradient of $NH_4CO_3$ buffer from 0.02–0.2M. Pure fractions were evaporated at 40° C. in high vacuo to dryness to give the pure product (79 mg).

NMR: ($CD_3OD$) δ=2.45 (m, 3H), 2.69 (m, 1H), 3.67 (m, 2H), 3.76 (m, 2H), 4.13 (t, 1H), 4.65 (m, 2H), 6.19 (m, 2H), 7.98 (td, 2H).

$P^{31}$ NMR: ($D_2O$) δ=−1.0(s)

5'-O-dimethoxytrityl-3'-[O-(3'-O-acetyl)-β-L-5-fluoro-2'-deoxyuridinyl]-α-L-5-fluoro-2'-deoxyuridine (25g)

The 3'-O-acetyl-β-D-5-fluoro-2'-deoxyuridine (0.19 g, 0.67 mmol) was dissolved in dry acetonitrile (20 ml). Sublimed 1H-tetrazole (70 mg) was added and the mixture was stirred under an argon atmosphere for 15 minutes. The solution of 21f (0.51 mg, 0.67 mmol), dissolved in 10 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (611 mg). This foam was used in the next step without further purification.

(3'-acetoxy-β-L-5-fluoro-2'-deoxyuridinyl)-α-L-5-fluoro-2'-deoxyuridine cyanoethyl phosphonate ester (26a)

The dimer, 25g (611 mg), was dissolved in 8 ml of THF and 2 ml of pyridine containing 0.2 ml of water. Iodine crystals (30 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated $NaHCO_3$ solution and brine. The organic layer was dried over $Na_2SO_4$, filtered and evaporated in vacuo. The residue was dissolved in 20 ml of 80% acetic acid/water solution and was stirred until the reaction was completed. The solvent was evaporated and the residue was purified on a silica gel column, using 10–15% $MeOH/CHCl_3$. Fractions containing one spot by TLC (10% $MeOH/CHCl_3$ Rf=0.35) were pooled and evaporated to give the pure product (200 mg).

3'-O-(β-L-5-fluoro-2'-deoxyuridinyl)-α-L-5-fluoro-2'-deoxyuridine (27g) [α-L β-L 5FUdR Dimer]

The o-protected dimer, 26g (200 mg) was treated with 20 ml of concentrated ammonia solution until the reaction is completed. The solvent was stripped off in vacuo and the residue was purified on DEAE cellulose ion exchange column using gradient of $NH_4CO_3$ buffer from 0.02–0.2M. Pure fractions were evaporated at 40° C. in high vacuo to dryness to give the pure product (134 mg).

NMR: ($D_2O$) δ=2.30 (m, 3H), 2.71 (m, 1H), 3.65 (m, 2H), 4.03 (m, 2H), 4.08 (t, 1H), 4.47 (m, 1H), 4.68 (m, 2H), 6.13 (d, 1H), 6.24 (td, 1H), 7.89 (d, 1H), 7.95 (d, 1H).

$P^{31}$ NMR: ($D_2O$) δ=0.32(s)

5'-O-(dimethoxytrityl)-β-L-2'-deoxyuridine-3'-N,N-diisopropylmethoxy phosphoramidite (21h)

The 5'-O-dimethoxytrityl-α-L-2'-deoxyuridine (1.0 g, 1.88 mmol) was dissolved in anhydrous dichloromethane (50 ml). N,N-diisopropylethylamine (1.31 ml, 7.55 mmol) was added through a septum, followed by chloro-N,N-diisopropylmethoxyphosphine (0.55 ml, 2.83 mmol), under an argon atmosphere. The reaction was stirred for 30 minutes. The solvent was evaporated and the residue was partitioned between an 80% EtOAc/triethylamine mixture and brine. The organic layer was washed with saturated $NaHCO_3$ solution and brine. The organic residue was evaporated to dryness and the residue was purified on a silica gel column using a mixture of dichloromethane, EtOAc and triethylamine (50:40:10; Rf=0.8). The product was isolated quantitatively as a yellow foam and it was used in the next step without further purification.

5'-O-dimethoxytrityl-3'-[O-(3'-O-acetyl)-β-D-5-fluoro-2'-deoxyuridinyl]-β-L-2'-deoxyuridine (25h)

The 3'-O-acetyl-β-D-5-fluoro-2'-deoxyuridine (0.54 g, 1.88 mmol) was dissolved in dry acetonitrile (50 ml). Sublimed 1H-tetrazole (200 mg) was added and the mixture was stirred under an argon atmosphere for 15 minutes. The solution of 21h (1.88 mmol), dissolved in 15 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (1.08 g). This foam was used in the next step without further purification.

(3'-acetoxy-β-D-5-fluoro-2'-deoxyuridinyl)-β-L-2'-deoxyuridine methyl phosphonate ester (26h)

The dimer, 25h (1.08 g), was dissolved in 15 ml of THF and 3 ml of pyridine containing 0.3 ml of water. Iodine crystals (100 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated $NaHCO_3$ solution and brine. The organic layer was dried over $Na_2SO_4$, filtered and evaporated in vacuo. The residue was dissolved in 25 ml of 80% acetic acid/water solution and was stirred until the reaction was completed. The solvent was evaporated and the residue was purified on a silica gel column, using 10–15% $MeOH/CHCl_3$. Fractions containing one spot by TLC (10% $MeOH/CHCl_3$ Rf=0.4) were pooled and evaporated to give the pure product (400 mg).

3'-O-(13-D-5-fluoro-2'-deoxyuridinyl)-g-L-2'-deoxyuridine (27h)

The O-protected dimer, 26h (400 mg) was treated with 100 ml of methnolic ammonia solution until the reaction is completed. The solvent was stripped off in vacuo and the residue was purified on DEAE cellulose ion exchange column using gradient of $NH_4CO_3$ buffer from 0.02–0.2M. Pure fractions were evaporated at 40° C. in high vacuo to dryness to give the pure product (175 mg).

NMR: ($D_2O$) δ=2.40 (m, 3H), 2.61 (m, 1H), 3.80 (m,2H), 4.10 (m, 2H), 4.18 (m,2H), 4.55 (m, 1H), 4.80 (m, 1H), 5.85 (d, 1H), 6.30 (q, 2H), 7.85 (d, 1H), 8.06 (d, 1H).

$P^{31}$ NMR: ($D_2O$) δ=0.20(s)

5'-O-dimethoxytri-tyl-$N^4$-benzoyl-2'-deoxy-β-L-cytidine (20i)

$N^4$-benzoyl-2'-deoxy-β-L-cytidine (0.8 g, 2.42) was dissolved in 50 ml of dry, distilled pyridine. To this solution was added 4,4'-dimethoxytrityl chloride (3.0 g, 8.85 mmol) and 4-dimethylamino pyridine (DMAP) (60 mg, 0.48 mmol). The mixture was stirred under an argon atmosphere for 16 hours. After this time, the pyridine was stripped off in vacuo. The residue was dissolved in EtOAc (100 ml). The organic layer was washed with water, saturated $NaHCO_3$, and brine. The organic layer was dried over $Na_2SO_4$, filtered and evaporated in vacuo to a residue which was purified on a silica gel column using 10% MeOH/CHCl$_3$. Pure fractions were pooled and evaporated to give the pure product as an off-white foam (1.49 g, (97% yield). Rf=0.48 in 10% MeOH/CHCl$_3$.

NMR: (CDCl$_3$-d$_6$) δ=2.3 (m, 1H), 2.75 (m, 2H), 3.42 (ddd, 2H), 3.80 (s, 6H), 4.15 (q, 2H), 4.52 (m, 1H), 6.30 (t, 1H), 6.82 (dd, 4H), 7.2–7.6 (m, Ar), 7.85 (d, 2H), 8.32 (d, 1H), 8.76 (br s, 1H).

5'-O-(dimethoxytrityl)-N$^4$-benzoyl-2'-deoxy-β-L-cytidine-3'-N,N-diisopropylmethyl phosphoramidite (21i)

The 5'-O-dimethoxytrityl-N$^4$-benzoyl-2'-deoxy-p3-L-cytidine (0.6 g, 0.95 mmol) was dissolved in anhydrous dichloromethane (50 ml). N,N-diisopropylethylamine (0.66 ml, 3.79 mmol) was added through a septum, followed by chloro-N,N-diisopropylmethoxyphosphine (0.28 ml, 1.42 mmol), under an argon atmosphere. The reaction was stirred for 30 minutes. The solvent was evaporated and the residue was partitioned between an 80% EtOAc/triethylamine mixture and brine. The organic layer was washed with saturated NaHCO$_3$ solution and brine. The organic residue was evaporated to dryness and the residue was purified on a silica gel column using a mixture of dichloromethane, EtOAc and triethylamine (60:30:10; Rf=0.8). The product was isolated quantitatively as a yellow foam and it was used in the next step without further purification.

5'-O-dimethoxytrityl-3'-[O-(3'-O-acetyl)-β-D-5-fluoro-2'-deoxyuridinyl]-N$^4$-benzoyl-2'-deoxy-β-L-cytidine (25U)

The 3'-O-acetyl)-β-D-5-fluoro-2'-deoxyuridine (0.23 g, 0.78 mmol) was dissolved in dry acetonitrile (30 ml). Sublimed 1H-tetrazole (110 mg) was added and the mixture was stirred under an argon atmosphere for 15 minutes. The solution of 21i (0.94 mmol), dissolved in 15 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (0.73 g). This foam was used in the next step without further purification.

(3'-acetoxy-β-D-5-fluoro-2'-deoxyuridinyl)-N$^4$-benzoyl-2'-deoxu-β-L-cytidine methyl phosphonate ester (26i)

The dimer, 25i (0.73 g), was dissolved in 20 ml of THF and 4 ml of pyridine containing 0.4 ml of water. Iodine crystals (100 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated NaHCO$_3$ solution and brine. The organic layer was dried over Na$_2$SO$_4$, filtered and evaporated in vacuo. The residue was dissolved in 25 ml of 80% acetic acid/water solution and was stirred until the reaction was completed. The solvent was evaporated and the residue was purified on a silica gel column, using 10–15% MeOH/CHCl$_3$. Fractions containing one spot by TLC (10% MeOH/CHCl$_3$ Rf=0.4) were pooled and evaporated to give the pure product (108 mg). 3'-O-(β-D-5-fluoro-2'-deoxyuridinyl)-2'-deoxy-O-L-cytidine (27i)

The O-protected dimer, 26i (108 mg) was treated with 100 ml of methnolic ammonia solution until the reaction is completed. The solvent was stripped off in vacuo and the residue was purified on DEAE cellulose ion exchange column using gradient of NH$_4$CO$_3$ buffer from 0.02–0.2M. Pure fractions were evaporated at 40° C. in high vacuo to dryness to give the pure product (56 mg).

NMR: (D$_2$O) δ=2.30 (m, 3H), 2.55 (m, 1H), 3.80 (m, 2H), 4.05 (m, 2H), 4.18 (m, 2H), 4.52 (m, 1H), 4.78 (m, 1H), 6.02 (d, 1H), 6.25 (m, 2H), 7.80 (d, 1H), 8.04 (d, 1H).

P$^{31}$ NMR: (D$_2$O) δ=0.05(s)

5'-O-dimethoxytrityl-3'-[O-(3'-O-acetyl)-N$^4$-benzoyl-2'-deoxy-D-L-cytidinyl)-β-D-5-fluoro-2'deoxyuridine (25j)

The 3'-O-acetyl-β-D-5-fluoro-2'-deoxyuridine (0.25 g, 0.67 mmol) was dissolved in dry acetonitrile (30 ml). Sublimed 1H-tetrazole (94 mg) was added and the mixture was stirred under an argon atmosphere for 15 minutes. The solution of 21j (0.51 g, 0.67 mmol), dissolved in 15 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (0.49 9). This foam was used in the next step without further purification.

(3'-acetoxy-N$^4$-benzoyl-2'-deoxy-(3-L-cytidinyl)-(β-D-5-fluoro-2'-deoxyuridinyl cyanoethyl phosphonate ester (26i)

The dimer, 25j (0.49 g), was dissolved in 8 ml of THF and 2 ml of pyridine containing 0.2 ml of water. Iodine crystals (30 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated NaHCO$_3$ solution and brine. The organic layer was dried over Na$_2$SO$_4$, filtered and evaporated in vacuo. The residue was dissolved in 20 ml of 80% acetic acid/water solution and was stirred until the reaction was completed. The solvent was evaporated and the residue was purified on a silica gel column, using 10–15% MeOH/CHCl$_3$. Fractions containing one spot by TLC (10% MeOH/CHCl$_3$ Rf=0.4) were pooled and evaporated to give the pure product (188 mg).

3'-O-(2'-deoxy-β-L-cytidinyl)-β-D-5-fluoro-2'-deoxyuridine (27i)

The O-protected dimer, 26j (188 mg) was treated with 100 ml of concentrated ammonia solution until the reaction is completed. The solvent was stripped off in vacuo and the residue was purified on DEAE cellulose ion exchange column using gradient of NH$_4$CO$_3$ buffer from 0.02–0.2M. Pure fractions were evaporated at 40° C. in high vacuo to dryness to give the pure product (105 mg).

NMR: (D$_2$O) δ=2.30 (m, 3H), 2.50 (m, 1H), 3.80 (m, 2H), 4.05 (m, 2H), 4.10 (m, 2H), 4.20 (m, 1H), 4.52 (m, 1H), 4.75 (m, 1H), 6.05 (d, 1H), 6.29 (q, 2H), 7.89 (d, 1H), 9.03 (d, 1H).

P$^{31}$NMR: (D$_2$O) δ=0.05(s)

5'-O-dimethoxytrityl-3'-[O-(3'-O-acetyl)-N$^4$-benzoyl-2'-deoxy-α-L-cytidinyl)-β-D-5-fluoro-2'-deoxyuridine (25k)

The 3'-O-acetyl-β-D-5-fluoro-2'-deoxyuridine (0.19 g, 0.51 mmol) was dissolved in dry acetonitrile (30 ml). Sublimed 1H-tetrazole (80 mg) was added and the mixture was stirred under an argon atmosphere for 15 minutes. The solution of 21k (0.45 g, 0.61 mmol), dissolved in 15 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (0.42 g). This foam was used in the next step without further purification.

(3'-acetoxy-N$^4$-benzoyl-2'-deoxy-α-L-cytidinyl)-β-D-5-fluoro-2'-deoxyuridinyl cyanoethyl phosphonate ester (26k)

The dimer, 25k (0.42 g), was dissolved in 10 ml of THF and 2 ml of pyridine containing 0.2 ml of water. Iodine crystals (45 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated NaHCO$_3$ solution and brine. The organic layer was dried over Na$_2$SO$_4$, filtered and evaporated in vacuo. The residue was dissolved in 25 ml of 80% acetic acid/water solution and was stirred until the reaction was completed. The solvent was evaporated and the residue was purified on a silica gel column, using 10–15% MeOH/CHCl$_3$. Fractions containing one spot by TLC (10% MeOH/CHCl$_3$ Rf=0.4) were pooled and evaporated to give the pure product (125 mg).

3'-O-(2'-deoxy-α-L-cytidinyl)-(3-D-5-fluoro-2'-deoxyuridine (27k)

The O-protected dimer, 26k (125 mg) was treated with 100 ml of concentrated ammonia solution until the reaction is completed. The solvent was stripped off in vacuo and the residue was purified on DEAE cellulose ion exchange column using gradient of NH$_4$CO$_3$ buffer from 0.02–0.2M). Pure fractions were evaporated at 40° C. in high vacuo to dryness to give the pure product (40 mg).

NMR: (D$_2$O) δ=2.15 (m, 1H), 2.35 (m, 1H), 2.60 (m, 1H), 2.71 (m, 1H), 3.81 (m, 2H), 3.97 (m, 2H), 4.22 (m, 1H), 4.52 (m, 2H), 6.02 (d, 1H), 6.15 (dd, 1H), 6.28 (t, 1H), 7.87 (d, 1H), 8.03 (d, 1H).

P$^{31}$NMR: (D$_2$O) δ=0.12(s)

EXAMPLE 5

Dimers Testing In Vitro in B16 Melanoma and P388 Leukemia and in Inhibition Assays Against 293 Processive Telomerase The biological effects of the dimers were compared with those of the monomeric 5-FUdR on P388 leukemia and B16 melanoma cell lines and in inhibition assays against 293 processive telomerase. Telomerase is a DNA-processive enzyme that is not expressed in normal somatic cells but generally only in germ-line cells and fetal cells. In many types of cancer cells, enzyme activity is reactivated, and others, telomerase inhibitors can therefore serve as a valuable new class of antineoplastic agents. The results are shown in Table 2.

TABLE 1

Inhibition of Tumor Cell Growth and Telomerase Activity by 5-FUdR Dinucleoside Monophosphates

| Compound | Growth Inhibition IC$_{50}$ (nM) | | Telomerase Inhibition (Mean ± SEM) |
|---|---|---|---|
| | P388 | B16 | % at 1 mN |
| β-D FUDR | 2.8 | 28 | 0 |
| α-L, β-D Dimer | 0.41 | 2.45 | 84 ± 11 |
| α-L FUDR | NT | 389,500 | NT |

NT = Not Tested

The results indicate that the prototype dimers inhibit the growth of murine-cultured leukemic L1210 and melanoma B16 cells with great potency (some IC$_{50}$ values of less than 1 nM.) The IC50 values are several times more potent than FUdR. These results are unexpected and thus these compounds are truly unique.

The preliminary results of the telomerase inhibition are also intriguing.

The α-L, β-D dimer inhibited the enzyme by 84% compared to control.

These data indicate that dimers containing an L-sugar have extremely interesting biological profiles and represent a novel class of potent antineoplastic agents. The activity profile of the L-dimers is different from that of the parent monomeric drug β-D-5FUdR.

The biological effects of the dimers were compared with those of the monomeric 5-FUdR on P388 leukemia and B16 melanoma cell lines. The results are shown in Table 2.

TABLE 3

In Vitro Testing Data

| | | IC$_{50}$ (nM) | |
|---|---|---|---|
| CODE # | COMPOUND | P388 | B16 |
| L-102 | β-D-FUdR, α-L-FUdR | 0.71 | 3.0 |
| L-103 | α-L-FUdR, β-D-FUdR | 0.57 | 2.45 |
| L-107 | α-L-dU, β-D-FUdR | 7.0 | 219 |
| L-108 | α-L-FUdR, α-L-FUdR | 22,200 | 52,200 |
| L-109 | β-L-FUDR, β-L-FUdR | 5860 | 45,900 |
| L-110 | β-L-FUdR, β-D-FUdR | 2.0 | 6.3 |
| L-111 | α-L-dC, β-D-FUdR | 0.7 | 5.0 |
| — | β-D-FUdR | 2.8 | 28 |

These data indicate that the dinucleoside monophosphate compounds containing β-D-5FUdR in conjunction with α-L or β-L-nucleosides show superior in vitro activities against murine P388 leukemia and B16 melanoma cell lines, as is evidenced by lower IC$_{50}$ values. This indicates that such nucleoside dimers may indeed be acting by mechanisms different from those of 5-FUdR or are metabolized and/or transported differently from 5-FUdR.

EXAMPLE 6

Determination of Thymidylate Synthase Activity and Its Inhibition in Intact L1210 Leukemia Cells In Vitro Thymidylate synthase is one suspected site of action of the compounds. Hence, the activity of selected compounds of the present invention, measured on thymidylate synthase activity measured in vitro, is a reliable indicium of the behavior of these compounds in in vivo systems.

Mouse leukemia L1210 cells are harvested from the cell culture flasks and the cell concentration is determined. The cells are then resuspended in the desired amount of the medium to give a stock concentration 5×10$^7$ cells/mL. Series of the dilution of the stock solution of the compounds to be tested are prepared (concentrations are ranged from 10$^8$ M to 10$^{-3}$ M). The solution of the compound to be tested in the desired concentration is pipetted into a microcentrifuge tube and incubated at 37° C. using a shaking water bath. The reaction is started by addition of [5-$^3$H]-2'-deoxycytidine (10 µL, concentration of the stock solution—10$^{-5}$ M) after a 30 or 60 min. preincubation with 80 µL of the cell suspension and allowed to proceed for 30 min. in a shaking water bath at 37° C. The reaction is terminated by adding 100 µL of the 10% charcoal in 4% HClO$_4$. The tubes are vigorously stirred by vortexing and then centrifuged for 10 min. in a Beckman Microfuge. The radioactivity of a 100 µL of supernatant fraction from each tube is counted in a Packard Tri-Carb (model 2450 or 3255) liquid scintillation spectrometer using a toluene based scintillation mixture.

The release of tritium is expressed as a percentage of the total amount of radioactivity added. $IC_{50}$ values determined from dose response curves represent the concentration of inhibitors required for 50% inhibition of the release of tritium. Table 3 below shows the results of the analysis of tritium release and determination of the $IC_{50}$.

TABLE 3

| Sample Code | Inhibition of Tritium Release, $IC_{50}$ ($\mu$M) |
| --- | --- |
| 5FUdR | 0.035 |
| L-102 | 0.035 |
| L-103 | 0.035 |
| L-107 | >100 |
| L-108 | >100 |
| L-109 | >100 |
| L-11O | 6 |
| L-111 | N/T |

EXAMPLE 7

In Vivo Testing of Dimers in P388 Leukemia B16 Melanoma

A. Experimental

1. P388 Leukemia

B6D2F1 mice received i.p. inocula of P388 murine leukemia cells prepared by removing ascites fluid containing P388 cells from tumored B6D2FI mice, centrifuging the cells, and then resuspending the leukemia cells in saline. Mice received $1\times10^6$ P388 cells i.p. on day 0. On day 1, tumored mice were treated with the dimers or vehicle control. The route of drug administration was i.p. and the schedule selected was dailyx5. The maximum tolerated doses (MTD) was 200 mg/kg for each dimer and was determined in initial dose experiments in non-tumored mice. In the actual experiments, L-103 was given at 100 mg/kg and 50 mg/kg.

2. B16 Melanoma

B6D2F1 mice received i.p. inocula of B16 murine melanoma brei prepared from B16 tumors growing s.c. in mice (day 0). On day 1, tumored mice were treated with the dimers or vehicle control. The route of drug administration was i.p. and the schedule selected was dailyx5. The maximum tolerated doses (MTD) was 200 mg/kg for each dimer and was determined in initial dose experiments in non-tumored mice. In the actual experiments, L-103 was given at 100 mg/kg and 50 mg/kg.

3. Survival Standard

The mean survival times of all groups were calculated, and results are expressed as mean survival of treated mice/mean survival of control mice (TIC)×100%. A TIC value of 150 means that the mice in the treated group lived 50% longer than those of the control group; this is sometimes referred to as the increase in life span, or ILS value.

In the P388 studies, mice that survive for 30 days are considered long term survivors or cures while in B16; mice that survive for 60 days are considered long term survivors or cures. The universally accepted cut-off for activity in both models, which has been used for years by the NCl, is TIC=125. Conventional use of B 16 and P388 over the years has set the following levels of activity: T/C<125, no activity; T/C=125–150, weak activity; T/C=150–200, modest activity; T/C=200–300, high activity; T/C>300, with long term survivors, excellent, curative activity.

B. Results

1. P388 Leukemia

L-103 demonstrated modest activity in the P388 leukemia in mice at all doses tested (Table 5). L-103 gave i.p. dailyx5 at doses of 100 mg/kg and 50 mg/kg resulted in TIC values of 149 and 144 respectively. Fluorodeoxyuridine (FUdR) was used as the positive drug control in this study; FUdR produced a T/C=164 in the P388 test (Table 4). All agents were well-tolerated in this experiment; there was little or no body weight loss and no toxic deaths were recorded.

TABLE 4

L-103 vs. Murine P388 Leukemia

| Group | n | Dose | Weight Change (Day 7) | T/C |
| --- | --- | --- | --- | --- |
| Control | (10) | 0.9% Saline | +9.1% | 100 |
| L-103 | (10) | 100 mg/kg | +1.5% | 149 |
| L-103 | (10) | 50 mg/kg | −1.6% | 144 |
| FUdR | (10) | 100 mg/kg | −2.7% | 164 |

2. B16 Melanoma

L-103 demonstrated modest activity against B16 melanoma implanted in mice (Table 6). L-103 (i.p.; dailyx5) gave T/C values of 139 and 134 respectively. The positive control drug FUdR resulted in modest efficacy in the B16 test; a T/C value of 135 was obtained (Table 5). All agents were well-tolerated, with little or no weight loss; no drug-related deaths occurred.

TABLE 5

L-103 vs. Murine B16 Leukemia

| Group | n | Dose | Weight Change (Day 7) | T/C |
| --- | --- | --- | --- | --- |
| Control | (10) | 0.9% Saline | +4.9% | 100 |
| L-103 | (10) | 100 mg/kg | +2.3% | 139 |
| L-103 | (10) | 50 mg/kg | +6.3% | 134 |
| FUdR | (10) | 100 mg/kg | −0.5% | 135 |

L-103 demonstrated modest activity against both the P388 and B16 experimental murine tumors at the two doses tested. L-103 was approximately as active as the positive control drug FUdR in the B16 test, and was somewhat less active than FUdR in the P388 test.

From the foregoing, the significance of L-sugar-based α- and β-enantiomeric nucleosides, nucleotides and their analogues as versatile, highly effective chemotherapeutic agents is apparent. Our results on derivatives of 5-FUdR show that L-5-FUdR-containing isomers are less toxic than those containing β-D-5FUdR, perhaps because they are not phosphorylated or transported as the latter. We have found that dimeric derivatives designed and prepared from α-L-5FUdR show very potent activity against P388 leukemia cells and B16 melanoma cell lines, exceeding that of β-D-5FUdR. They appear to have unusual mechanisms of action, including inhibition of telomerase.

EXAMPLE 8

In Vivo Activity of Nucleoside Analogs

The different activity of the dimers is dependent on the structure of the second nucleoside.

The following plausible pathways for metabolic activation and/or mode of action of the dimer molecules tested are that:

(1) Dimer may act as a new chemical entity without hydrolysis of the phosphate or pro-phosphate bond between the two monomeric units;

(2) Hydrolysis to L-nucleoside and FUdR nucleotide may occur, in which case the dimer is a prodrug. The L-nucleoside is used for protection
and to increase the bioavailability of β-D-FUdR monophosphate.

It is also important to note that hydrolysis can take place intracellularly as well as outside the cell.

In the last decade, monumental efforts have been directed toward the synthesis of oligonucleotide analogs with altered phosphodiester linkage.

The goal was to improve the stability of duplex and triplex formation, to improve the cellular uptake and to decrease the rate of degradation of oligonucleotides by endo and exo nucleases which cleave the phosphodiester linkage. We selected one such chemical modification for our study. As a consequence, several dimers with phosphorothioate linkage between two nucleosides were synthesized and tested. The phosphorothioate comprises a sulfur-for-oxygen substitution at phosphorus of the phosphodiester linkage (for the structure of the corresponding dimers see Appendix 1). It has been shown (M. Matsukura, K. Shinozuka, G. Zon, H. Mitsuya, M. Reitz, J. S. Cohen, L. M. Neckers, Proc. Natl. Acad. Sci. USA. 84, 7706 (1987)) that the S homologues are more resistant to cellular nucleases and are readily taken up by cells. Several oligonucleotides of this type are currently in clinical studies (ISIS Pharmaceuticals and others).

EXAMPLE 8

Synthesis of $N^6$-Benzoyl-3'-deoxy-β-D-adenosine

To a stirring solution of 3'-deoxyadenosine (2.0 g, 7.96 mmol) in pyridine (80 ml) chilled in an ice bath, ClSiMe$_3$ (5.0 ml, 39.8 mmol) was added dropwise and stirred for 30 minutes. Benzoyl chloride (3.7 ml, 31.84 mmol) was then added dropwise and the reaction mixture was stirred at room temperature for two hours. This was cooled in an ice bath and water (16 ml) was added dropwise. 15 minutes later concentrated NH$_4$OH (16 ml) was added to give a solution approximately 2M in ammonia. After 30 minutes the solvent was evaporated and the residue was dissolved in water and washed with ether. The water layer was concentrated and the compound was crystallized from water as white solid (2.32 g. 82%).

EXAMPLE 9

Synthesis of $N^6$-Benzoyl-5'-O-(di p-methoxytrityl)-3'-deoxy-β-D-adenosine

To a solution of compound $N^6$-Benzoyl-3'deoxy-β-D-adenosine 1(2.32 g, 6.53 mmol) in pyridine (100 ml) was added 4,4'-dimethoxytrityl chloride (3.32 g, 9.79 mmol) and DMAP (0.24 g, 1.96 mmol) and stirred at room temperature for 2 hours under argon. To complete the reaction, additional DMTCI (0.5 g) was added and stirred for another 2 hours. The reaction was quenched with the addition of MeOH (5 ml) and the solvent was evaporated. The residue was dissolved in EtOAc, washed with water, NaHCO$_3$ and brine. After drying over Na$_2$SO$_4$, the EtOAc layer was evaporated and the crude compound was purified on a silica gel column using 80% EtOAc/CHCl$_3$ as solvent to give pure compound 2 (4.33 g, 83%) as a white foam.

EXAMPLE 10

Synthesis of $N^6$-Benzoyl-2'-O-acetoxy-(3-D-3'-deoxyadenosine

To a solution of $N^6$-Benzoyl-5'-O-(di p-methoxytrityl)-3'-deoxy-β-D-adenosine (4.3 g, 6.58 mmol) in pyridine (100 ml) acetic anhydride (1 ml, 9.87 mmol), and DMAP (0.08 g, 0.65 mmol) was added and stirred at room temperature for 15 minutes. Then the solvent was evaporated and the residue was dissolved in EtOAc, washed with water, NaHCO$_3$, brine and dried over NA$_2$SO$_4$. After the evaporation of EtOAc, then the crude material was dissolved in 80% AcOH (50 ml) and stirred at room temperature for one hour. Then the solvent was evaporated and coevaporated with tolune and purified on a silica gel column using 3–5% MeOH/CHCl$_3$ to give pure $N^6$-Benzoyl-2'-O-acetoxy-β-D-3-deoxyadenosine (2.11 g, 81%) as a foam.

Example 11

Synthesis of β-L-dU, Cordycepin Dimer (L-150)

β-L-dU (1.0 g, 4.38 mmol) was dissolved in dry pyridine (50 ml), to this solution was added 4,4'-dimethoxytrityl chloride (1.78 g, 5.25 mmol) and DMAP (0.1 g, 0.87 mmol). This was stirred under argon at room temperature for 2 hours and quenched with MeOH (5 ml). The solvent was evaporated, the residue was dissolved in EtOAc, washed with water, NaHCO$_3$ and brine. After drying and evaporation of the solvent, the crude material was purified on a silica gel column using 60–80% EtOAc/CHCl$_3$ as solvent to give pure 5'-O-Dimethoxytrityl-β-L-2'-deoxyuridine (2.2 g, 94.8%) as white foam.

Dimethoxytrityl-β-L-2'-deoxyuridine (1.5 g, 2.83 mmol) was dissolved in anhydrous dichloromethane (50 ml). N,N-diisopropylethylamine (2.0 ml, 11.3 mmol) was added uner argon followed by 2'-cyanoethyl-N,N-diisopropylchlorophosphoramidite (0.82 ml, 3.68 mmol). The reaction was stirred for 30 minutes and the solvent was evaporated. The residue was dissolved in 80% EtOAc/Et$_3$N (75 ml) and washed with water, NaHCO$_3$ and brine. The organic layer was evaporated and purified on a short silica gel column using a mixture of EtOAc, CH$_2$Cl$_2$ and ET$_3$N (40:50:10) to give 5'-O-Dimethoxytrityl-β-L-2'-deoxyuridine-3'-N, N-diisopropylcyanoethyl phosphoramidite in quantitative yield.

5'-O-Dimethoxytrityl-3'-[O-(2'-O-acetyl)-$N^6$-benzoyl-β-D-3'-deoxy adenosinyl]-2'-deoxy-β-L-uridine cyanoethyl phosphite ester (7).

To a solution of compound 5'-O-Dimethoxytrityl-β-L-2'-deoxyuridine-3'-N, N-diisopropylcyanoethyl phosphoramidite (2.83 mmol) in anhydrous acetonitrile (60 ml), $N^6$-Benzoyl-2'-O-acetoxy-β-D-3-deoxyadenosine (1.12 g, 2.83 mmol) in acetonitrile (40 ml) was added and stirred for 10 minutes under argon. To this solution, sublimed 1H-tetrazole (0.6 g, 8.5 mmol) was added and stirred over night. The solvent was evaporated and the residue was triturated with 70% EtOAc/ether and filtered. The filtrate was evaporated to give 5'-O-Dimethoxytrityl-3'-[O-(2'-O-acetyl)-$N^6$-benzoyl-β-D-3'-deoxy adenosinyl]-2'-deoxy-β-L-uridine cyanoethyl phosphite ester as a foam and this was used in the next step without further purification.

The 5'-O-Dimethoxytrityl-3'-[O-(2'-O-acetyl)-$N^6$-benzoyl-β-D-3'-deoxy adenosinyl]-2'-deoxy-β-L-uridine cyanoethyl phosphite ester was dissolved in THF (24 ml), pyridine (6 ml) and water (0.6 ml). Iodine crystals (1.0 g) were added portion wise until the iodine color persists. The reaction mixture was stirred for another 15 minutes and the excess iodine was removed by the addition of saturated sodium thiosulfate. The solvent was evaporated and the residue was dissolved in EtOAc and washed with water, NaHCO$_3$ and brine. EtOAc layer was evaporated and the residue was dissolved in 80% acetic acid/water solution (40 ml) and stirred for 1 hour. Then the solvent was evaporated and the crude product was purified on a silica gel column using 8–15% MeOH/CHCl$_3$ as solvent to give pure (2'-Acetoxy-N$^6$-benzoyl-3'-deoxy-β-D-adenosinyl)-β-L-2'-deoxyuridinyl cyanoethyl phosphate ester (0.75 g) as a foam.

The dimer (2'-Acetoxy-N$^6$-benzoyl-3'-deoxy-β-D-adenosinyl)-β-L-2'-deoxyuridinyl cyanoethyl phosphate ester (0.75 g) was treated with ammoniun hydroxide solution (100 ml) over night. The solvent was evaporated and the residue was purified on DEAE Cellulose ion exchange column using gradient of NH$_4$HCO$_3$ buffer (0.05–0.2M). The pure fractions were collected and lyophillized to give pure 3'-O-(3'-deoxy-β-D-adenosinyl)-β-L-2'-deoxyuridine (L-150)(0.486 g) as white solid.

EXAMPLE 12

Synthesis of β-L-dA, Cordycepin dimer (L-151)

To a stirring solution of 2'-deoxy-β-L-adenosine (2.05 g, 8.16 mmol) in pyridine (75 ml) chilled in an ice bath, ClSiMe$_3$ (5.17 ml, 40.8 mmol) was added dropwise and stirred for 30 minutes. Benzoyl chloride (4.7 ml, 40.8 mmol) was then added dropwise and the reaction mixture was stirred at room temperature for two hours. This was cooled in an ice bath and water (15 ml) was added dropwise. 15 minutes later concentrated NH$_4$OH (15 ml) was added to give a solution approximately 2 M in ammonia. After 30 minutes the solvent was evaporated and the residue was dissolved in water and washed with ether. The water layer was concentrated and the N$^6$-benzoyl-2'-deoxy-β-L-adenosine was crystallized from water as white solid (2.48 g, 85.8%).

To a solution of N$^6$-benzoyl-2'-deoxy-β-L-adenosine (2.48 g, 6.98 mmol) in pyridine (100 ml) was added 4,4'-dimethoxy trityl chloride (3.55 g, 10.47 mmol) and DMAP (0.25 g, 2.09 mmol) and stirred at room temperature for 2 hours under argon. To complete the reaction, additional DMTCl (1.3 g) was added and stirred for another 2 hours. The reaction was quenched with the addition of MeOH (5 ml) and the solvent was evaporated. The residue was dissolved in EtOAc, washed with water, NaHCO$_3$ and brine. After drying over Na$_2$SO$_4$, the EtOAc layer was evaporated and the crude compound was purified on a silica gel column using 3–5% MeOH/CHCl, as solvent to give pure N$^6$-benzoyl-5'-O-(di-p-methoxy trityl)-2'-deoxy-β-L-adenosine (3.42 g, 74.5%) as pale yellow foam.

N$^6$-benzoyl-5'-O-(di-p-methoxy trityl)-2'-deoxy-β-L-adenosine (1.64 g, 2.5 mmol) was dissolved in anhydrous dichloromethane (50 ml). N,N-diisopropylethylamine (1.75 ml, 10.0 mmol) was added under argon followed by 2'-cyanoethyl-N,N-diisopropylchlorophosphoramidite (0.8 ml, 3.25 mmol). The reaction was stirred for 30 minutes and the solvent was evaporated. The residue was dissolved in 80% EtOAc/Et$_3$N (75 ml) and washed with water, NaHCO$_3$ and brine. The organic layer was evaporated and purified on a short silica gel column using a mixture of EtOAc, CH$_2$CL$_2$ and Et$_3$N (40:50: 10) to give N'-Benzoyl-5'-O-(dimethoxytrityl)-β-L-2'-deoxyadenosine-3'-N,N-diisopropylcyanoethyl phosphoramidite in quantitative yield.

To a solution of N$^6$-Benzoyl-5'-O-(dimethoxytrityl)-β-L-2'-deoxyadenosine-3'-N,N-diisopropylcyanoethyl phosphoramidite (2.5 mmol) in anhydrous acetonitrile (60 ml), N$^6$-Benzoyl-2'-O-acetoxy-β-D-3'-deoxyadenosine (0.94 g, 2.36 mmol) in acetonitrile (40 ml) was added and stirred for 10 minutes under argon. To this solution, sublimed 1H-tetrazole (0.5 g, 7.2 mmol) was added and stirred over night. The solvent was evaporated and the residue was triturated with 70% EtOAc/ether and filtered. The filtrate was evaporated to give N$^6$-Benzoyl-5'-O-(dimethoxytrityl)-3'-[O-(2'-O-acetyl)-N$^6$-benzoyl-β-D-3-deoxy adenosinyl]-2'-deoxy-β-L-adenosine cyanoethyl phosphite ester as a foam and this was used in the next step without further purification.

The dimer N$^6$-Benzoyl-5'-O-(dimethoxytrityl)-3'-[O-(2'-O-acetyl)-N$^6$-benzoyl-β-D-3-deoxy adenosinyl]-2'-deoxy-β-L-adenosine cyanoethyl phosphite was dissolved in THF (24 ml), pyridine (6 ml) and water (0.6 ml). Iodine crystals (0.63 g) were added portion wise until the iodine color persists. The reaction mixture was stirred for another 15 minutes and the excess iodine was removed by the addition of saturated sodium thiosulfate. The solvent was evaporated and the residue was dissolved in EtOAc and washed with water, NaHCO$_3$ and brine. EtOAc layer was evaporated and the residue was dissolved in 80% acetic acid/water solution (50 ml) and stirred for 1 hour. Then the solvent was evaporated and the crude product was purified on a silica gel column using 5–10% MeOH/CHCl$_3$ as solvent to give pure (2'-Acetoxy-N$^6$-benzoyl-3'-deoxy-β-D-adenosinyl)-N$^6$-benzoyl-β-L-2'-deoxyadenosinyl cyanoethyl phosphate ester (0.97 g) as a foam.

The dimer (2'-Acetoxy-N$^6$-benzoyl-3'-deoxy-β-D-adenosinyl)-N$^6$-benzoyl-β-L-2'-deoxyadenosinyl cyanoethyl phosphate ester (0.97 g) was treated with ammonium hydroxide solution (100 ml) over night. The solvent was evaporated and the residue was purified on DEAE Cellulose ion exchange column using gradient of NH$_4$HCO$_3$ buffer (0.05–0.2M). The pure fractions were collected and lyophillized to give pure compound 3'-O-(3'-deoxy-β-D-adenosinyl)-β-L-2'-deoxyadenosine (15) (L-151) (0.55 g) as white solid.

EXAMPLE 13

Synthesis of α-L-dU, Cordycepin Dimer (L-152)

α-L-dU (1.04 g, 4.5 mmol) was dissolved in dry pyridine (50 ml), to this solution was added 4, 4'-dimethoxytrityl chloride (2.4 g, 6.86 mmol) and DMAP (0.11 g, 0.91 mmol). This was stirred under argon at room temperature for 2 hours and quenched with MeOH (5mL). The solvent was evaporated, the residue was dissolved in EtOAc, washed with water, NaHCO$_3$ and brine. After drying and evaporation of the solvent, the crude material was purified on a silica gel column using 3–5% MeOH/CHCl$_3$ as solvent to give pure 5'-O-Dimethoxytrityl-α-L-2'-deoxyuridine (2.4 g., 99%) as white foam.

5'-O-Dimethoxytrityl-α-L-2'-deoxyuridine (1.73 g, 3.26 mmol) was dissolved in anhydrous dichloromethane (30 ml), N,N-diisopropylethylamine (2.3 ml, 13.04 mmol) was added under argon followed by 2'-cyanoethyl-N,N-diisopropylchlorophosphoramidite (0.95 ml, 4.23 mmol). The reaction was stirred for 30 minutes and the solvent was evaporated. The residue was dissolved in 80% EtOAc/Et$_3$N (75 ml) and washed with water, NaHCO$_3$ and brine. The organic layer was evaporated and purified on a short silica gel column using a mixture of EtOAc, CH$_2$CL$_2$ and Et$_3$N (40:50:10) to give 5'-O-Dimethoxytrityl-α-L-2'-deoxyuridine-3'-N, N-diisopropylcyanoethyl phosphoramidite (2.26 g, 95%) as a foam.

To a solution of 5'-O-Dimethoxytrityl-α-L-2'-deoxyuridine-3'-N, N-diisopropylcyanoethyl phosphoramidite (2.26 g, 3.09 mmol) in anhydrous acetonitrile (60 ml), $N^6$-Benzoyl-2'-O-acetoxy-β-D-3'-deoxyadenosine (1.35 g, 3.4 mmol) in acetonitrile (40 ml) was added and stirred for 10 minutes under argon. To this solution, sublimed 1H-tetrazole (0.65 g, 8.5 mmol) was added and stirred over night. The solvent was evaporated and the residue was triturated with 70% EtOAc/ether and filtered. The filtrate was evaporated to give 5'-O-Dimethoxytrityl-3'-[O-(2'-O-acetyl)-$N^6$-benzoyl-β-D-3'-deoxyadenosinyl]-2'-deoxy-α-L-uridine cyanoethyl phosphite ester as a foam and this was used in the next step without further purification.

The dimer 5'-O-Dimethoxytrityl-3'-[O-(2'-O-acetyl)-$N^6$-benzoyl-β-D-3'-deoxyadenosinyl]-2'-deoxy-α-L-uridine cyanoethyl phosphite ester was dissolved in THF (24 ml), pyridine (6 ml) and water (0.6 ml). Iodine crystals (0.7 g) were added portion wise until the iodine color persists. The reaction mixture was stirred for another 15 minutes and the excess iodine was removed by the addition of saturated sodium thiosulfate. The solvent was evaporated and the residue was dissolved in EtOAc and washed with water, $NaHCO_3$ and brine. EtOAc layer was evaporated and the residue was dissolved in 80% acetic acid/water solution (50 ml) and stirred for 1 hour. Then the solvent was evaporated and the crude product was purified on a silica gel column using 8–15% MeOH/$CHCl_3$ as solvent to give pure (2'-Acetoxy-$N^6$-Benzoyl-3'-deoxy-β-D-adenosinyl)-α-L-2'-deoxyuridinyl cyanoethyl phosphate ester (1.29 g) as a foam.

3'O-(3'-deoxy-β-D-adenosinyl)-α-L-2'-deoxyuridine (6) (L-152)

The dimer (2'-Acetoxy-$N^6$-Benzoyl-3'-deoxy-β-D-adenosinyl)-α-L-2'-deoxyuridinyl cyanoethyl phosphate ester (1.29 g) was treated with ammonium hydroxide solution (100 ml) over night, The solvent was evaporated and the residue was purified on DEAE Cellulose ion exchange column using gradient of $NH_4HCO_3$ buffer (0.05–0.2M). The pure fractions were collected and lyophillized to give pure 3'-O-(3'-deoxy-β-D-adenosinyl)-α-L-2'-deoxyuridine (L-152) (0.856 g) as white solid.

EXAMPLE 14

Synthesis of β-L-dC, Cordycepin Dimer (L-153)

To a solution of β-L-dCBz (1.7 g, 5.22 mmol) in pyridine (100 ml) was added 4,4'-dimethoxy trityl chloride (2.65 g, 7.83 mmol) and DMAP (0.13 g, 1.04 mmol) and stirred at room temperature for 2 hours under argon.

To complete the reaction, additional DMTCI (0.9 g) was added and stirred for another 2 hours. The reaction was quenched with the addition of MeOH (5 ml) and the solvent was evaporated. The residue was dissolved in EtOAc, washed with water, $NaHCO_3$ and brine. After drying over $Na_2SO_4$, the EtOAc layer was evaporated and the crude compound was purified on a silica gel column using 3–5% MeOH/$CHCl_3$ as solvent to give pure $N^4$-Benzoyl-5'-O-(di-p-methoxytrityl)-2'-deoxy-β-L-cytidine (2.98 g, 90%) as pale yellow foam.

$N^4$-Benzoyl-5'-O-(dimethoxytrityl)-β-L-2'-deoxycytidine-3'-N,N-diisopropylcyanoethyl phosphoramidite (3)

$N^4$-Benzoyl-5'-O-(di-p-methoxy trityl)-2'-deoxy-β-L-cytidine (1.7 g, 2.68 mmol) was dissolved in anhydrous dichloromethane (50 ml), N,N-diisopropylethylamine (1.9 ml, 10.72 mmol) was added under argon followed by 2'-cyanoethyl-N, N-diisopropylchlorophosphoramidite (0.85 ml, 3.5 mmol). The reaction was stirred for 30 minutes and the solvent was evaporated. The residue was dissolved in 80% EtOAc/$Et_3N$ (75 ml) and washed with water, $NaHCO_3$ and brine. The organic layer was evaporated and purified on a short silica gel column using a mixture of EtOAc, $CH_2Cl_2$ and $Et_3N$ (30:60:10) to give $N^4$-Benzoyl-5'-O-(dimethoxytrityl)-β-L-2'-deoxycytidine-3'-N,N-diisopropylcyanoethyl phosphoramidite (2.06 g, 92%) as a foam.

To a solution of $N^4$-Benzoyl-5'-O-(dimethoxytrityl)-β-L-2'-deoxycytidine-3'-N,N-diisopropylcyanoethyl phosphoramidite (2.06 g, 2.47 mmol) in anhydrous acetonitrile (100 ml),$N^6$-benzoyl-2'-O-acetoxy-β-D-3'-deoxyadenosine (1.08 g, 2.72 mmol) in acetonitrile (40 ml) was added and stirred for 10 minutes under argon. To this solution, sublimed 1H-tetrazole (0.52 g, 7.4 mmol) was added and stirred over night. The solvent was evaporated and the residue was triturated with 70% EtOAc/ether and filtered.

The filtrate was evaporated to give $N^4$-Benzoyl-5'-O-dimethoxytrityl-3'-[O-(2'-O-acetyl)-$N^6$-benzoyl-β-D-3'-deoxy adenosinyl]-2'-deoxy-β-L-cytidine cyanoethyl phosphite ester as a foam and this was used in the next step without further purification. The dimer $N^4$-Benzoyl-5'-O-dimethoxytrityl-3'-[O-(2'-O-acetyl)-$N^6$-benzoyl-β-D-3'-deoxy adenosinyl]-2'-deoxy-β-L-cytidine cyanoethyl phosphite ester was dissolved in THF (24 ml), pyridine (6 ml) and water (0.6 ml). Iodine crystals (0.55 g) were added portion wise until the iodine color persists. The reaction mixture was stirred for another 15 minutes and the excess iodine was removed by the addition of saturated sodium thiosulfate.

The solvent was evaporated and the residue was dissolved in EtOAc and washed with water, $NaHCO_3$ and brine. EtOAc layer was evaporated and the residue was dissolved in 80% acetic acid/water solution (50 ml) and stirred for 1 hour. Then the solvent was evaporated and the crude product was purified on a silica gel column using 5–10% MeOH/$CHCl_3$ as solvent to give pure compound (2'-Acetoxy-$N^6$-benzoyl-3'-deoxy-β-D-adenosinyl)-$N^4$-Benzoyl-β-L-2'-deoxycitydinyl cyanoethyl phosphate ester (1.46 g) as afoam.

3'-O-(3'-deoxy-β-D-adenosinyl)-β-L-2'-deoxycytidine (6) (L-153)

The dimer (2'-Acetoxy-$N^6$-benzoyl-3'-deoxy-β-D-adenosinyl)-$N^4$-Benzoyl-β-L-2'-deoxycitydinyl cyanoethyl phosphate ester (1.46 g) was treated with ammoniun hydroxide solution (100 ml) over night. The solvent was evaporated and the residue was purified on DEAE Cellulose ion exchange column using gradient of $NH_4HCO_3$ buffer (0.05–0.2M). The pure fractions were collected and lyophillized to give pure 3'-O-(3'-deoxy-β-D-adenosinyl)-β-L-2'-deoxycytidine (L-153) (0.81 g) as white solid.

EXAMPLE 15

Synthesis of α-L-dC, Cordycepin dimer (L-154)

To a solution of α-L-dC (1.6 g, 4.88 mmol) in pyridine (100 ml) was added 4, 4'-dimethoxy trityl chloride (2.43 g, 7.2 mmol) and DMAP (0.13 g, 1.04 mmol) and stirred at room temperature for 2 hours under argon. To complete the reaction, additional DMTCI (1.0 g) was added and stirred for another 2 hours. The reaction was quenched with the addition of MeOH (5 ml) and the solvent was evaporated. The residue was dissolved in EtOAc, washed with water $NaHCO_3$ and brine. After drying over $Na_2SO_4$, the EtOAc layer was evaporated and the crude compound was purified on a silica gel column using 3–5% MeOH/$CHCl_3$ as solvent to give pure $N^4$-Benzoyl-5'-O-(di-p-methoxytrityl)-2'-deoxy-α-L-cytidine (2.34 g, 76%) as pale yellow foam.

$N^4$-Benzoyl-5'-O-(di-p-methoxy trityl)-2'-deoxy-α-L-cytidine (1.84 g, 2.9 mmol) was dissolved in anhydrous dichloromethane (50 ml). N,N-diisopropylethylamine (2.0 ml, 11.6 mmol) was added under argon followed by 2'-cyanoethyl-N, N-diisopropylchlorophosphoramidite (0.85 ml, 3.5 mmol).

The reaction was stirred for 30 minutes and the solvent was evaporated. The residue was dissolved in 80% EtOAc/Et$_3$N (75 ml) and washed with water, NaHCO$_3$ and brine. The organic layer was evaporated and purified on a short silica gel column using a mixture of EtOAc, hexane and Et$_3$N (50:40:10) to give N$^4$-Benzoyl-5'-O-(dimethoxytrityl)-α-L-2'-deoxycytidine-3'-N,N-diisopropylcyanoethyl phosphoramidite (2.01 g, 83%) as a foam.

To a solution of compound N$^4$-Benzoyl-5'-O-(dimethoxytrityl)-α-L-2'-deoxycytidine-3'-N,N-diisopropylcyanoethyl phosphoramidite (2.01 g, 2.4 mmol) in anhydrous acetonitrile (100 ml), N$^6$-Benzoyl-2'-O-acetoxy-β-D-3'-deoxyadenosine (1.05 g, 2.65 mmol) in acetonitrile (40 ml) was added and stirred for 10 minutes under argon. To this solution, sublimed 1-H-tetrazole (0.5 g, 7.2 mmol) was added and stirred over night. The solvent was evaporated and the residue was triturated with 70% EtOAc/ether and filtered. The filtrate was evaporated to give N$^4$-Benzoyl-5'-O-(dimethoxytrityl)-3'-[O-(2'-acetyl)-N$^6$-Benzoyl-β-D-3'-deoxy adenosinyl]-2'-deoxy-α-L-cytidine cyanoethyl phosphite ester as a foam and this was used in the next step without purification.

The dimer N$^4$-Benzoyl-5'-O-(dimethoxytrityl)-3'-[O-(2'-acetyl)-N$^6$-Benzoyl-β-D-3'-deoxy adenosinyl]-2'-deoxy-α-L-cytidine cyanoethyl phosphite ester was dissolved in THF (24 ml), pyridine (6 ml) and water (0.6 ml). Iodine crystals (0.5 g) were added portion wise until the iodine color persists. The reaction mixture was stirred for another 15 minutes and the excess iodine was removed by the addition of saturated sodium thiosulfate. The sulfate was evaporated and the residue was dissolved in EtOAc and washed with water, NaHCO$_3$ and brine. EtOAc layer was evaporated and the residue was dissolved in 80% acetic acid/water solution (50 ml) and stirred for 1 hour. Then the solvent was evaporated and the crude product was purified on a silica gel column using 5–10% MeOH/CHCl$_3$ as solvent to give pure (2'-Acetoxy-N$^6$-Benzoyl-3'-deoxy-β-D-adenosinyl)-N$^4$-Benzoyl-α-L-2-deoxycitydinyl cyanoethyl phosphate ester (1.8 g) as a foam.

The dimer (2'-Acetoxy-N$^6$-Benzoyl-3'-deoxy-β-D-adenosinyl)-N$^4$-Benzoyl-α-L-2-deoxycitydinyl cyanoethyl phosphate ester (1.8 g) was treated with ammonium hydroxide solution (100 ml) over night, The solvent was evaporated and the residue was purified on DEAE Cellulose ion exchange column using gradient of NH$_4$HCO$_3$ buffer (0.05–0.2M). The pure fractions were collected and lyophillized to give pure 3'-O-(3'-deoxy-β-D-adenosinyl)-α-L-2'-deoxycytidine (L-154) (1.08 g) as white solid.

EXAMPLE 16

Synthesis of α-L-dA, Cordycepin Dimer (L-155)

To a stirring solution of 2'-deoxy-α-L-adenosine (2.05 g, 8.16 mmol) in pyridine (75 ml) chilled in an ice bath, ClSiMe$_3$ (5.17 ml, 40.8 mmol) was added dropwise and stirred for 30 minutes. Benzoyl chloride (4.7 ml, 40.8 mmol) was then added dropwise and the reaction mixture was stirred at room temperature for two hours. This was cooled in an ice bath and water (15 ml) was added dropwise, 15 minutes later concentrated NH$_4$OH (15 ml) was added to give a solution approximately 2M in ammonia. After 30 minutes the solvent was evaporated and the residue was dissolved in water and washed with ether. The water layer was concentrated and the N$^6$-Benzoyl-2'-deoxy-α-L-adenosine crystallized from water as white solid (2.48 g, 85.8%).

To a solution of compound N$^6$-Benzoyl-2'-deoxy-α-L-adenosine (2.48 g, 6.98 mmol) in pyridine (100 ml) was added 4, 4'-dimethoxy trityl chloride (3.55 g, 10.47 mmol) and DMAP (0.25 g, 2.09 mmol) and stirred at room temperature for 2 hours under argon. To complete the reaction, additional DMTCI (1.3 g) was added and stirred for another 2 hours. The reaction was quenched with the addition of MeOH (5 ml) and the solvent was evaporated. The residue was dissolved in EtOAc, washed with water, NaHCO$_3$ and brine. After drying over Na$_2$SO$_4$, the EtOAc layer was evaporated and the crude compound was purified on a silica gel column using 3–5% MeOH/CHCl$_3$ as solvent to give pure N$^6$-Benzoyl-5'-O-(di-p-methoxy trityl)-2'-deoxy-α-L-adenosine (3.42 g, 74.5%) as pale yellow foam.

N$^6$-Benzoyl-5'-O-(di-p-methoxy trityl)-2'-deoxy-α-L-adenosine (1.64 g, 2.5 mmol) was dissolved in anhydrous dichloromethane (50 ml). N,N-diisopropylethylamine (1.75 ml, 10.0 mmol) was added under argon followed by 2'-cyanoethyl-N, N-diisopropylchlorophosphoramidite (0.8 ml, 3.25 mmol). The reaction was stirred for 30 minutes and the solvent was evaporated. The residue was dissolved in 80% EtOAc/Et$_3$N (75 ml) and washed with water, NaHCO$_3$ and brine. The organic layer was evaporated and purified on a short silica gel column using a mixture of EtOAc, CH$_2$Cl$_2$ and Et$_3$N (40:50: 10) to give N$^6$-Benzoyl-5'-O-(dimethoxytrityl)-α-L-2'-deoxyadenosine-3'-N,N-diisopropylcyanoethyl phosphoramidite in quantitative yield.

To a solution of N$^6$-Benzoyl-5'-O-(dimethoxytrityl)-α-L-2'-deoxyadenosine-3'-N,N-diisopropylcyanoethyl phosphoramidite(2.5 mmol) in anhydrous acetonitrile (60 ml), N$^6$-Benzoyl-3'-O-acetoxy-β-D-2'-deoxyadenosine (0.94 g, 2.36 mmol) in acetonitrile (40 ml) was added and stirred for 10 minutes under argon. To this solution, sublimed 1H-tetrazole (0.5 g, 7.2 mmol) was added and stirred overnight. The solvent was *4' evaporated and the residue was triturated with 70% EtOAct ether and filtered. The filtrate was evaporated to give N$^6$-Benzoyl-5'-O-dimethoxytrityl-3'-[O-(2'-)-acetyl)-N$^6$-benzoyl-β-D-3'-deoxy adenosinyl]-2'-deoxy-α-L-adenosine cyanoethyl phosphite ester as a foam and this was used in the next step without further purification.

The dimer N$^6$-Benzoyl-5'-O-dimethoxytrityl-3'-[O-(2'-)-acetyl)-N$^6$-benzoyl-β-D-3'-deoxy adenosinyl]-2'-deoxy-α-L-adenosine cyanoethyl phosphite ester was dissolved in THF (24 ml), pyridine (6 ml) and water (0.6 ml). Iodine crystals (0.63 g) were added portion wise until the iodine color persists. The reaction mixture was stirred for another 15 minutes and the excess iodine was removed by the addition of saturated sodium thiosulfate. The solvent was evaporated the residue was dissolved in EtOAc and washed with water, NaHCO$_3$ and brine. EtOAc layer was evaporated and the residue was dissolved in 80% acetic acid/water solution (50 ml) and stirred for 1 hour. Then the solvent was evaporated and the crude product was purified on a silica gel column using 5–10% MeOH/CHCl$_3$ as solvent to give pure compound (2'-Acetoxy-N$^6$-benzoyl-3'-deoxy-β-D-adenosinyl)-N$^6$-benzoyl-α-L-2'-deoxyadenosinyl cyanoethyl phosphate ester (0.97 g) as a foam.

The dimer (2'-Acetoxy-N$^6$-benzoyl-3'-deoxy-β-D-adenosinyl)-N$^6$-benzoyl-α-L-2'-deoxyadenosinyl cyanoethyl phosphate ester(0.97 g) was treated with ammonium hydroxide solution (100 ml) overnight. The solvent was evaporated and the residue was purified on DEAE Cellulose ion exchange column using gradient of NH$_4$HCO$_3$ buffer (0.05–0.2M). The pure fractions were collected and lyophillized to give pure 3'-O-(3'-deoxy-β-D-adenosinyl)-β-L-2'-deoxyadenosine (0.55 g)(L-1 55) as white solid.

EXAMPLE 17

Synthesis of β-L-dA, β-D-dA (L-210)

To a stirring solution of 2'-deoxy-β-L-adenosine (2.05 g, 8.16 mmol) in pyridine (75 ml) chilled in an ice bath, ClSiMe$_3$ (5.17 ml, 40.8 mmol) was added dropwise and stirred for 30 minutes. Benzoyl chloride (4.7 ml, 40.8 mmol) was then added dropwise and the reaction mixture was stirred at room temperature for two hours. This was cooled in an ice bath, and water (15 ml) was added dropwise. 15 minutes later concentrated NH$_4$OH (15 ml) was added to give a solution approximately 2M in ammonia. After 30 minutes, the solvent was evaporated and the residue was dissolved in water and washed with ether. The water layer was concentrated, and the N$^6$-Benzoyl-2'-deoxy-β-L-adenosine was crystallized from water as white solid (2.48 g, 85.8%).

To a solution of N$^6$-Benzoyl-2'-deoxy-β-L-adenosine (2.48 g, 6.98 mmol) in pyridine (100 ml) was added 4,4'-dimethoxy trityl chloride (3.55 g, 10.47 mmol) and DMPA (0.25 g, 2.09 mmol) and stirred at room temperature for 2 hours under argon. To complete the reaction, additional DMTCl (1.3 g) was added and stirred for another 2 hours. The reaction was quenched with the addition of MeOH (5 ml), and the solvent was evaporated. The residue was dissolved in EtOAc, washed with water, NaHCO$_3$ and brine. After drying over Na$_2$SO$_4$, the EtOAc layer was evaporated and the crude compound was purified on a silica gel column using 3/5% MeOH/CHCl$_3$ as solvent to give pure N$^6$-Benzoyl-5'-O-(di-p-methoxy trityl)-2'-deoxy-β-L-adenosine (3.42 g, 74.5%) as pale yellow foam.

N$^6$-Benzoyl-5'-O-(di-p-methoxy trityl)-2'-deoxy-β-L-adenosine(1.71 g, 2.61 mmol) was dissolved in anhydrous dichloromethane (50 ml). N,N-diisopropylethylamine (1.8 ml, 10.34 mmol) was added under argon followed by 2'-cyanoethyl-N,N-diisopropylchlorophosphoramidite (1.0 ml, 4.47 mmol). The reaction was stirred for 30 minutes, and the solvent was evaporated. The residue was dissolved in 80% EtOAc/Et$_3$N (75 ml) and washed with water, NaHCO$_3$ and brine. The organic layer was evaporated and purified on a short silica gel column using a mixture of EtOAc, hexane and Et$_3$N (50:40:10) to give N$^6$-Benzoyl-5'-O-(dimethoxytrityl)-β-L-2'-deoxyadenosine-3'-N,N-diisopropylcyanoethyl phosphoramidite(1.87 g, 84%) as a foam.

To a solution of N$^6$-Benzoyl-5'-O-(dimethoxytrityl)-β-L-2'-deoxyadenosine-3'-N,N-diisopropylcyanoethyl phosphoramidite(1.87 g, 2.18 mmol) in anhydrous acetonitrile (60 ml), N$^6$-Benzoyl-3'-O-acetoxy-β-D-2'-deoxyadenosine (0.95 g, 2.4 mmol) in acetonitrile (40 ml) was added and stirred for 10 minutes under argon. To this solution, sublimed 1H-tetrazole (0.46 g, 6.6 mmol) was added and stirred overnight. The solvent was evaporated, and the residue was triturated with 70% EtOAc/ether and filtered. The filtrate was evaporated to give N$^6$-Benzoyl-5'-O-dimethoxytrityl-3'-[O-(3'-O'acetyl)-N$^6$-benzoyl-β-D-2'-deoxy adenosinyl]-2'-deoxy-β-L-adenosine cyanoethyl phosphite ester as a foam, and this was used in the next step without further purification.

The dimer N$^6$-Benzoyl-5'-O-dimethoxytrityl-3'-[O-(3'-O'acetyl)-N$^6$-benzoyl-β-D-2'-deoxy adenosinyl]-2'-deoxy-β-L-adenosine cyanoethyl phosphite ester was dissolved in THF (24 ml), pyridine (6 ml) and water (0.6 ml). Iodine crystals (0.5 g) were added portion wise until the iodine color persists. The reaction mixture was stirred for another 15 minutes, and the excess iodine was removed by the addition of saturated sodium thiosulfate. The solvent was evaporated, and the residue was dissolved in EtOAc and washed with water, NaHCO$_3$ and brine. EtOAc layer was evaporated, and the residue was dissolved in 80% acetic acid/water solution (50 ml) and stirred for 1 hour. Then the solvent was evaporated, and the crude product was purified on a silica gel column using 5–10% MeOH/CHCl$_3$ as solvent to give pure compound (3'-Acetoxy-N$^6$-benzoyl-2'-deoxy-β-D-adenosinyl)-N$^6$-benzoyl-β-L-2'-deoxyadenosinyl cyanoethyl phosphate ester (0.13 g) as a foam.

The dimer (3'-Acetoxy-N$^6$-benzoyl-2'-deoxy-β-D-adenosinyl)-N$^6$-benzoyl-β-L-2'-deoxyadenosinyl cyanoethyl phosphate ester(1.3 g) was treated with ammonium hydroxide solution (100 ml) overnight. The solvent was evaporated, and the residue was purified on DEAE Cellulose ion exchange column using gradient of NH$_4$HCO$_3$ buffer (0.05–0.2M). The pure fractions were collected and lyophillized to give pure 3'-O-(2'-deoxy-β-D-adenosinyl)-β-L-2'-deoxyadenosine (L-210) (0.640 g) as white solid.

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

One skilled in the art readily appreciates that the patent invention is well adapted to carry out the objectives and obtain the ends and advantages mentioned as well as those inherent therein. Dimers, pharmaceutical compositions, treatments, methods, procedures and techniques described herein are presently representative of the preferred embodiments and are intended to be exemplary and are not intended as limitations of the scope. Changes therein and other uses will occur those skilled in the art which are encompassed within the spirit of the invention or defined by the scope of the pending claims.

What is claimed is:

1. A pharmaceutical composition comprised of a nucleoside dimer having the formula:

wherein X is a moiety PO$_4$ or S=PO$_3$;

wherein R$_1$ and R$_2$ are the same or different nucleosides;

wherein R$_1$ and R$_2$ are selected from the group consisting of β-D-deoxyfluorouridine, α-L-deoxyfluorouridine, β-L-deoxyfluorouridine, α-L-deoxycytidine, β-L-deoxycytidine, β-L-deoxyuridine, β-L-deoxyguanosine, β-L-deoxyadenosine, α-L-deoxyadenosine and nitrobenzylthionosine; and wherein R$_1$ and R$_2$ are attached to X through —OH groups.

2. The pharmaceutical composition according to claim 1 wherein R$_1$ is β-D-deoxyfluorouridine.

3. The pharmaceutical composition according to claim 1 wherein R$_1$ is α-L-deoxyfluorouridine.

4. The pharmaceutical composition according to claim 1 wherein R$_1$ is β-L-deoxyfluorouridine.

5. The pharmaceutical composition according to claim 1 wherein R$_1$ is α-L-deoxycytidine.

6. The pharmaceutical composition according to claim 1 wherein R$_1$ is β-L-deoxycytidine.

7. The pharmaceutical composition according to claim 1 wherein $R_1$ is β-L-deoxyguanosine.

8. The pharmaceutical composition according to claim 1 wherein $R_1$ is β-L-deoxyguanosine.

9. The pharmaceutical composition according to claim 1 wherein $R_1$ is β-L-deoxyadenosine.

10. The pharmaceutical composition according to claim 1 wherein $R_1$ is α-L-deoxyadenosine.

11. The pharmaceutical composition according to claim 1 wherein $R_1$ is nitrobenzylthionosine.

12. A pharmaceutical composition of a nucleoside dimer comprising: β-D-deoxyfluorouridine, β-L-deoxyadenosine, and a suitable moiety for linking the two said nucleosides selected from the group consisting of $PO_4$ or $S=PO_3$.

* * * * *